US007803946B2

(12) United States Patent
Haley et al.

(10) Patent No.: US 7,803,946 B2
(45) Date of Patent: Sep. 28, 2010

(54) TUNABLE PHENYLACETYLENE HOSTS

(76) Inventors: Michael M. Haley, 1025 Satre St., Eugene, OR (US) 97401; Darren W. Johnson, 1510 Cal Young Rd., Eugene, OR (US) 97401; Orion B. Berryman, 1047 W. 18th Pl., Eugene, OR (US) 97405; Charles A. Johnson, 1253 Franklin Blvd., Eugene, OR (US) 97403; Calden N. Stimpson, 2381 Jefferson St., Eugene, OR (US) 97405

( * ) Notice: Subject to any disclaimer, the term of this patent is extended or adjusted under 35 U.S.C. 154(b) by 145 days.

(21) Appl. No.: 11/957,243

(22) Filed: Dec. 14, 2007

(65) Prior Publication Data
US 2008/0167472 A1 Jul. 10, 2008

Related U.S. Application Data

(60) Provisional application No. 60/875,055, filed on Dec. 14, 2006.

(51) Int. Cl.
C07D 213/38 (2006.01)
C07D 213/40 (2006.01)

(52) U.S. Cl. .................. 546/257; 546/265; 546/335; 546/337

(58) Field of Classification Search .................. 546/257, 546/265, 335, 337
See application file for complete search history.

(56) References Cited

OTHER PUBLICATIONS

Walters et. al. "Experimental Studies of Light-Induced Charge Transfer and Charge Redistribution in (X2-Bipyridine)Rel(CO)3Cl Complexes" Inorganic Chemistry 2002, 41, 2909-2919.*
Carroll, Calden N. et al; "Protonation activates anion binding and alters binding selectivity in new inherently fluorescent 2,6-bis(2-anilinoethynyl)pyridine bisureas"; Chemical Communications, 2009, 2520-2522; Copyright 2009 The Royal Society of Chemistry; Cambridge, United Kingdom; 3 pages.
Dash, Jyotirmayee et al; "Diarylethynyl amides that recognize the parallel conformation of genomic promoter DNA G-quadruplexes"; Journal of the American Chemical Society (2008), 130(47), 15950-15956; Web publication date Nov. 4, 2008; 8 pages.
Dash, Jyotirmayee et al; "G-quadruplex recognition by bis-indole carboxamides"; Chemical Communications, 2008 (26) 3055-3057; Copyright 2008 The Royal Society of Chemistry; Cambridge, United Kingdom; 3 pages.
Berryman, Orion B. et al; "Water and hydrogen halides serve the same structural role in a series of 2+2 hydrogen-bonded dimers based on 2,6-bis(2-anilinoethynyl)pyridine sulfonamide receptors"; Angewandte Chemie, International Edition (2008), 47(1), 117-120; Copyright 2008 Wiley-VCH GmbH & Co. KGaA, Weinheim; 4 pages.
Jia, Wen-Li et al; "Novel Phosphorescent Cyclometalated Organotin(IV) and Organolead(IV) Complexes of 2,6-Bis(2'-indolyl)pyridine and 2,6-Bis[2'-(7-azaindolyl)]pyridine"; Organometallics (2003), 22, 4070-4078; Copyright 2003 American Chemical Society; 9 pages.
Pucher, Niklas et al; "Structure-Activity Relationship in D-π-A-π-D-Based Photoinitiators for the Two-Photon-Induced Photopolymerization Process"; Macromolecules; in press, received Apr. 9, 2009; revised Jul. 17, 2009; 10 pages; American Chemical Society.
Ferrara, Joseph D. et al; "Synthesis and Characterization of the First Transition-Metal Complex of 1,2:5,6:9,10-Tribenzocyclododeca-1,5,9-triene-3,7,11-triyne"; J. Am. Chem. Soc., 1985, 107, 6719-6721; Copyright 1985 American Chemical Society; 3 pages.
Butler, Ian R. et al; "Bipyridylacetylenes 1: the synthesis of some bipyridylacetylenes via the palladium-catalyzed coupling of acetylenes with 2,2'-dibromobipyridyl, and the single crystal X-ray structure of 6,6'-bisphenylethynyl-2,2'-bipyridine"; Can. J. Chem. vol. 69, 1991 1117-1123; 7 pages.
Droz, Anne Sophie et al; "Synthesis of highly-functionalised, optically active disaccharide receptors by sequential aryl-alkyne cross- and oxidative acetylenic homo-coupling"; J. Chem. Soc., Perkin Trans. 1, 2000, 4224-4226; Copyright 2000 The Royal Society of Chemistry; 3 pages.
Ferrara, Joseph D. et al; "Synthesis and Characterization of a Copper(I) Triflate Complex of 1,2:5,6:9,10-Tribenzocyclododeca-1,5,9-triene-3,7,11-triyne"; Organometallics 1987, 6, 676-678; Copyright 1987 American Chemical Society; 3 pages.
Leininger, Stefan et al; "Self-Assembly of Discrete Cyclic Nanostructures Mediated by Transition Metals"; Chem. Rev. 2000, 100, 853-908; Copyright 2000 American Chemical Society; 56 pages.
Gerhardt, Warren W. et al; "Supramolecular cruciforms"; Chemical Communications 2006 (20), 2141-2143; Cambridge, United Kingdom; copyright 2006 The Royal Society of Chemistry; 3 pages.
Mcgrier, Psaras L. et al; "Hydroxy-cruciforms"; Chemical Communications 2007, (21), 2127-2129; Cambridge, United Kingdom; copyright 2007 The Royal Society of Chemistry; 3 pages.
Gerhardt, Warren W. et al; "Controlling polymer properties through dynamic metal-ligand interactions: supramolecular cruciforms made easy"; Chem. Eur. J. 2007, 13(16), 4467-4474; copyright 2007 Wiley-VCH Verlag GmbH & Co. KGaA, Weinstein; 8 pages.
Hauck, Martina, et al; "Phenothiazine Cruciforms: Synthesis and Metallochromic Properties"; Journal of Organic Chemistry (2007), 72(18), 6714-6725; copyright 2007 American Chemical Society; 12 pages.
Wilson, James N. et al; "Switching of Intramolecular Charge Transfer in Cruciforms: Metal Ion Sensing"; Journal of the American Chemical Society (2005), 127(12), 4124-4125; copyright 2005 American Chemical Society; 2 pages.

(Continued)

*Primary Examiner*—Rita J Desai
*Assistant Examiner*—David K O'Dell
(74) *Attorney, Agent, or Firm*—Kolisch Hartwell, PC

(57) ABSTRACT

Disclosed herein is a class of tunable phenylacetylene compounds as well as compositions and methods for their use as host compounds for ligand binding. In certain examples the hosts report binding events by exhibiting altered spectroscopic properties, such as different fluorescent emission spectra.

7 Claims, No Drawings

OTHER PUBLICATIONS

Zucchero, Anthony J. et al; "Cruciforms as functional fluorophores: Response to protons and selected metal ions"; Journal of the American Chemical Society (2006), 128(36), 11872-11881; copyright 2006 American Chemical Society; 10 pages.

Johnson, Charles A., II et al; "Synthesis and characterization of pyridine- and thiophene-based platinacyclynes"; Journal of Organometallic Chemistry 691 (2006) 413-421; Available online Oct. 25, 2005; 9 pages.

Johnson, Charles A., II et al; "Aryl-Acetylene Scaffolding as Receptors in Supramolecular Chemistry"; presentation through Department of Chemistry & Materials Science Institute of the University of Oregon; 2007; 26 pages.

* cited by examiner

TUNABLE PHENYLACETYLENE HOSTS

CROSS REFERENCE TO RELATED APPLICATION

This application claims the benefit of the earlier filing date of U.S. Provisional 60/875,055 filed Dec. 14, 2006, which is incorporated herein by reference in its entirety.

ACKNOWLEDGMENT OF GOVERNMENT SUPPORT

This invention was made with government support under Grant Nos. CHE-0414175 and CHE-0718242 awarded by the National Science Foundation. The government has certain rights in the invention.

FIELD

Disclosed herein is a class of tunable phenylacetylene compounds as well as compositions and methods for their use as host compounds for ligand binding.

BACKGROUND

The synthesis of new molecules designed to bind or sense and report the presence of a particular substrate is an area of chemistry that is attracting attention. There exists a general lack of ligand-specific host molecules, such as specific hosts for toxic ions and small molecules of interest. There also is a dearth of specific hosts that report binding events, for example by exhibiting a spectral shift upon binding, such as an altered fluorescent response. In fact, structures of fluorescent coordination complexes are generally poorly understood, which makes the rational design of functional hosts and sensors a challenging undertaking.

The detection of ionic species, in particular the selective detection of a particular ionic species in the presence of another is difficult. The detection of anionic species is a particular challenge, as anions are difficult to bind and are generally larger than cations leading to a smaller charge-to-radius ratio.

SUMMARY

Disclosed herein are host or receptor compounds that bind targets of interest. In one embodiment the compounds bind ions, such as metal ions. In particular, toxic metal ions, including anions and cations are bound by embodiments of the disclosed host compounds.

In one embodiment the host compounds and salts thereof have the formula

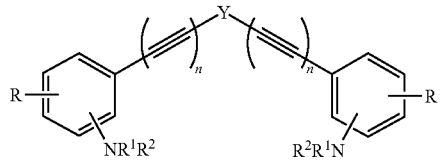

wherein Y represents an optionally substituted aromatic group;
n is 1 or 2;
R is H or lower alkyl;
$R^1$ is H, lower alkyl or aralkyl;
$R^2$ is selected from H, acyl, aralkyl, phosphonyl, —$SO_2R^3$; —$(R^4)C(O)R^5$; —$N(R^6)C(O)OR^7$ and —$N(R^8)C(O)NR^9R^{10}$;
$R^3$; $R^4$; $R^5$; $R^6$; $R^7$; $R^8$, $R^9$ and $R^{10}$ independently are selected from H, lower alkyl, aralkyl and aryl.

Exemplary compounds exhibit shifts in their spectral properties upon ligand binding. Accordingly, also disclosed are methods for using the host compounds to detect targets of interest, including neutral, cationic and anionic targets.

The foregoing and other objects, features, and advantages of the invention will become more apparent from the following detailed description.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Acyl" refers group of the formula RC(O)— wherein R is an organic group.

The term "aliphatic" includes alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers an aliphatic group that is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" refers to the formula —C(O)NRR', wherein R and R' independently can be a hydrogen, alkyl, alkenyl, alkynyl, aryl, aralkyl, cycloalkyl, halogenated alkyl, or heterocycloalkyl group described above.

The term "aralkyl" refers to an alkyl group that is substituted with one or more aryl groups (described below). A particular example of an aralkyl group is a benzyl group.

The term "aryl" refers to any carbon-based aromatic group including, but not limited to, benzene, naphthalene, etc. The term "aromatic" also includes "heteroaryl groups," which are defined as aromatic groups that have at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carbonate" refers to a group of the formula —OC(O)O—. Likewise, as used herein the term "carbamate" refers to a group of the formula —OC(O)N(R)—, wherein R is H, or an aliphatic group, such as a lower alkyl group or an aralkyl group.

"Carboxyl" refers to a —COOH radical. Substituted carboxyl refers to —COOR where R is aliphatic, heteroaliphatic, alkyl, heteroalkyl, or a carboxylic acid or ester.

"Optional" or "optionally" means that the subsequently described event or circumstance can but need not occur, and that the description includes instances where said event or circumstance occurs and instances where it does not. Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "phosphoryl" refers to moieties of the formula —P(O)OR—, wherein R may be H, an aliphatic or aromatic moiety, a cation or a lone pair of electrons. Phosphoryl moieties may be further substituted to form phosphoramidates, phosphates and phosphonates.

The term "sulfonyl" refers to the radical —SO$_2$—. The sulfonyl group can be further substituted with a variety of groups to form, for example, sulfonic acids, sulfonamides, sulfonate esters and sulfones.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure.

The disclosed host compounds are useful, inter alia, as ion binding compounds. By way of example, specific anions bound by the disclosed compounds include, but are not limited to, toxic metal anions, halide anions, carboxylates, phosphates, sulfates, oxalates, terephthalates, phospholipids, nucleotides, oligonucleotides, DNA, RNA, anionic polyoxometalates, or oxoanions such as pertechnetate.

The structural formulas provided herein include salts of the illustrated compounds. Such salts can be formed when disclosed host compounds possess at least one basic group that can form acid-base salts with acids. Examples of basic groups present in exemplary disclosed host compounds include amino groups or imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Similarly, salts can be formed when disclosed host compounds possess at least one acidic group that can form acid-base salts with bases. Examples of acidic groups present in exemplary disclosed host compounds include carboxylic acid moieties and sulfonamide groups. Compounds that include at least one acidic group can form an acid-base salts with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. In addition, quaternary ammonium counterions also can be used.

Additionally, the structural formulas herein are intended to cover, where applicable, solvated as well as unsolvated forms of the compounds. "Solvate" refers to a compound physically associated with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compounds, methanol associated compounds, and the like. "Hydrate" is a solvate wherein the solvent molecule(s) is/are H$_2$O. Solvate complexes may be described in shorthand form for example as $(1.H_2O)_2$, which refers to a hydrate, more specifically a 2+2 complex of compound 1 with water.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

In one embodiment, the disclosed host compounds have the formula

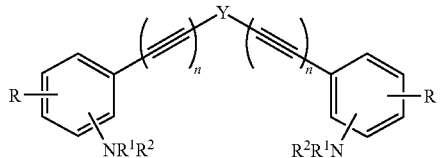

wherein Y represents an optionally substituted aromatic group;

n is 1 or 2;

R is H or lower alkyl;

$R^1$ is H, lower alkyl or aralkyl;

$R^2$ is selected from H, acyl, aralkyl, phosphonyl, —$SO_2R^3$; —($R^4$)C(O)$R^5$; —N($R^6$)C(O)$OR^7$ and —N($R^8$)C(O)$NR^9R^{10}$;

$R^3$; $R^4$; $R^5$; $R^6$; $R^7$; $R^8$ $R^9$ and $R^{10}$ independently are selected from H, lower alkyl, aralkyl and aryl.

In embodiments wherein n is 1, the disclosed host compounds can be represented by the formula

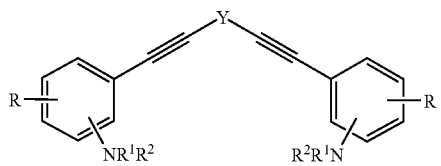

With reference to the generic formulas above, a guest molecule can bind in the cavity created between the aromatic group "Y" and the functional groups appended to the aniline nitrogens "$R^1$ and $R^2$".

With continued reference to the general formula above, such compounds can be cyclized, for example, by covalently linking an $R^1$ or $R^2$ group to another. Thus, macrocyclic compounds can be formed by linking an $R^1$ or $R^2$ group to another $R^1$ or $R^2$ group on a different aniline nitrogen.

With continued reference to the formula above, the R group can be selected for several purposes. Typically, R is selected to tune or tailor the electronics of the ring by selecting an electron donating or electron withdrawing and/or conjugated group. In other examples, R is selected for detection purposes, or, for instance, to affect the solubility of the overall molecule. Suitable R groups include, without limitation those listed in Table 1.

| Substituent | Hammett constant ($\sigma_{para}$) |
| --- | --- |
| —H | 0.00 |
| —$OCH_3$ | −0.27 |
| —$CH_3$ | −0.04 |
| —$CH_2CH_3$ | −0.05 |
| —$C(CH_3)_3$ | |
| —F | 0.06 |
| —Cl | 0.23 |
| —Br | 0.23 |
| —I | 0.18 |
| —$CF_3$ | 0.54 |
| —$OCF_3$ | |
| —$NO_2$ | 0.78 |

-continued

| Substituent | Hammett constant ($\sigma_{para}$) |
| --- | --- |
| —O—C6H5 | |
| —$N_3$ | |
| —CN | 0.66 |
| —OH | −0.37 |
| —$NH_2$ | −0.66 |
| —N($CH_3$)$_2$ | −0.83 |
| —C(O)OH | 0.45 |
| —$SO_3^-$ | 0.09 |

The group "Y" can be any aromatic group, but typically Y comprises a heteroaromatic group. For example, in one embodiment, the group "Y" employed was a pyridyl group. Additional exemplary Y groups include, without limitation, bipyridyl, pyridinyl, pyrazinyl, pyrimidinyl, pyrrole, imidazole, triazole, thiophene, thiazole, furyl and oxazolyl groups. By way of example, such Y groups can be selected from

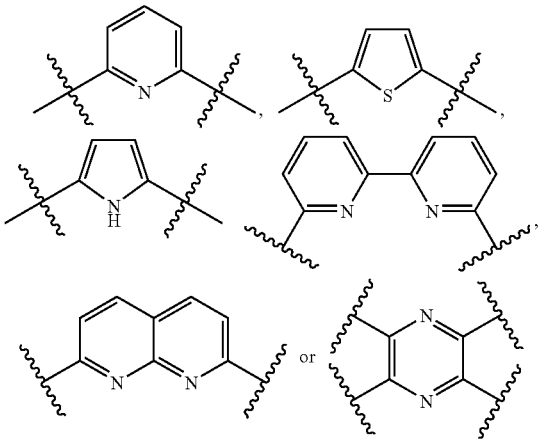

In other embodiments, Y is selected from, without limitation, the following heteroaromatic groups

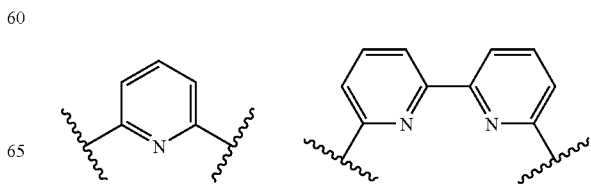

-continued

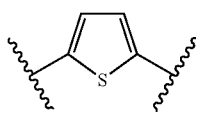

Other appropriate Y groups can be identified by those of skill in the art using the guidance provided by the present disclosure and by considering factors such as: the ring topology, bond angles, geometry of coordination to the guest, and number of available hydrogen bonds.

In one embodiment, the disclosed host compounds have the structure:

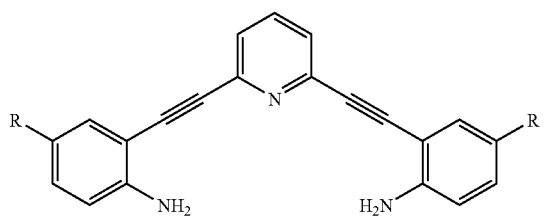

wherein R is H, aliphatic, such as lower alkyl (including optionally substituted lower alkyl), aralkyl, aryl, sulfonyl, phosphonyl, phosphate, sulfate, —XC(O)OR$^6$ and —XC(O)NR$^7$R$^8$; wherein X is optional and if present is selected from the group consisting of —O—, —N(R$^9$)— or —S—; R$^6$ is selected from lower alkyl, aralkyl and aryl; and R$^7$, R$^8$ and R$^9$ independently are selected from H, lower alkyl, aralkyl and aryl.

In one embodiment, Y is a hydrogen bond acceptor and/or donor. For example when Y is pyridyl, it is a hydrogen bond acceptor at high (basic) pH and a hydrogen bond donor when it is in its conjugate acid form at low pH.

In one embodiment the disclosed host compounds have the structure:

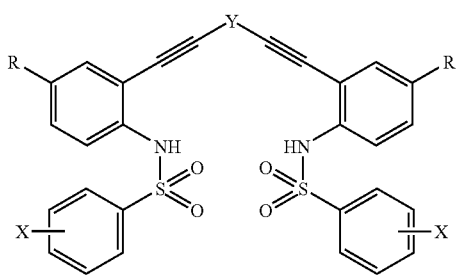

wherein X is selected from halogen, —OR$^{11}$, nitro, sulfonyl, phosphonyl, phosphate, sulfate, or optionally substituted lower alkyl;

and R$^{11}$ is H, acyl or optionally substituted lower alkyl. When X includes an optionally substituted lower alkyl moiety, optional substitutions include, without limitation hydroxy and sulfide moieties.

Particular examples of sulfonamide host compounds can be represented by the formula

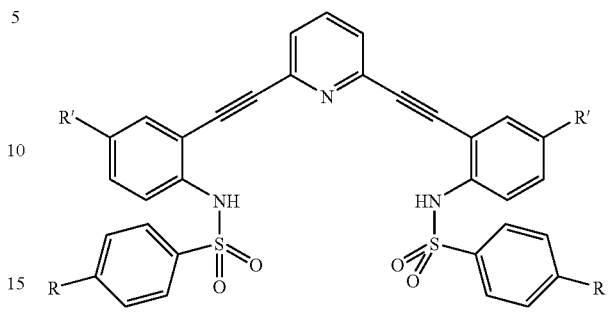

wherein R is selected from —OR, —SR, —Me, halo, such as —Br, and —NO$_2$, and wherein R' is, for each occurrence selected from H, lower alkyl and acyl. With reference to such sulfonamide compounds, they include acidic NH groups, which are good hydrogen bond donors.

Particular examples of such sulfonamide compounds have the formula

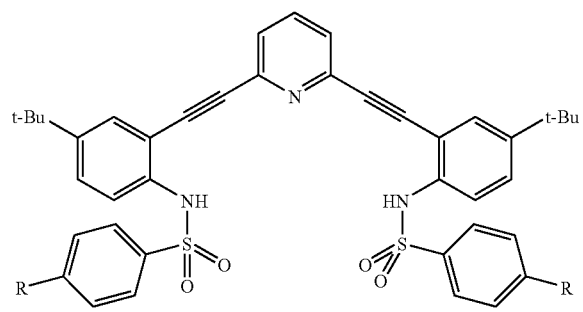

Additional embodiments include urea compounds, such as those of the formula:

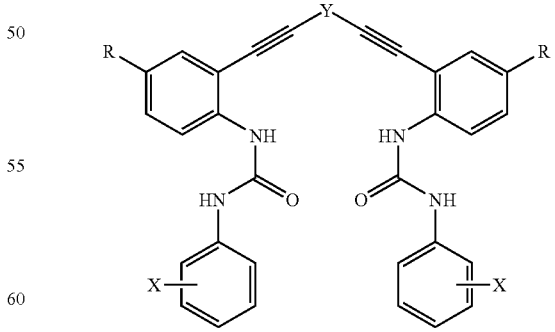

wherein R is lower alkyl and X is H, —OR$^{11}$, halogen, lower alkyl, phosphonyl, phosphate, sulfonyl or sulfate; and R$^{11}$ is H, acyl or optionally substituted lower alkyl.

Other urea compounds have the formula

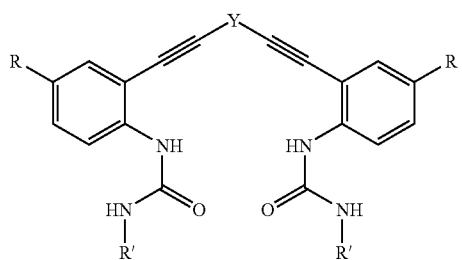

wherein R' is H or optionally substituted lower alkyl, such as methyl, t-butyl, octyl and the like. In one aspect, certain urea compounds can be represented by the formula

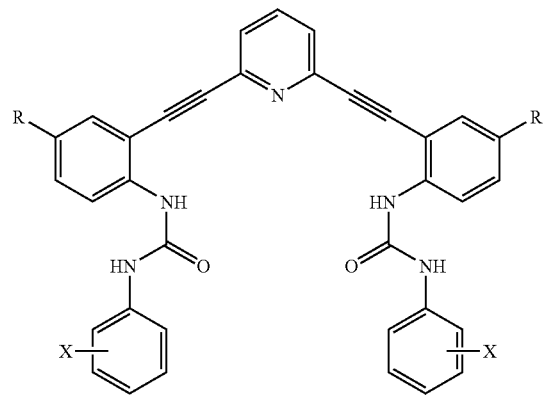

One such compound had the formula

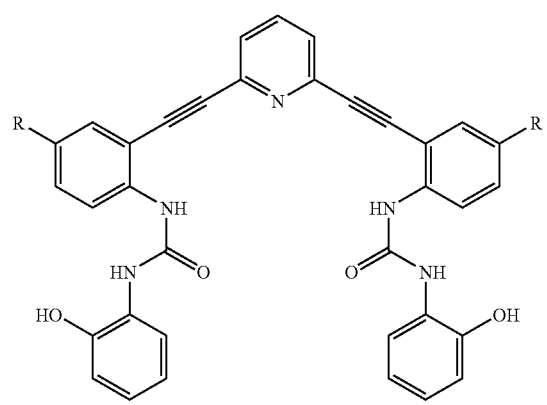

A second such urea compound has the formula

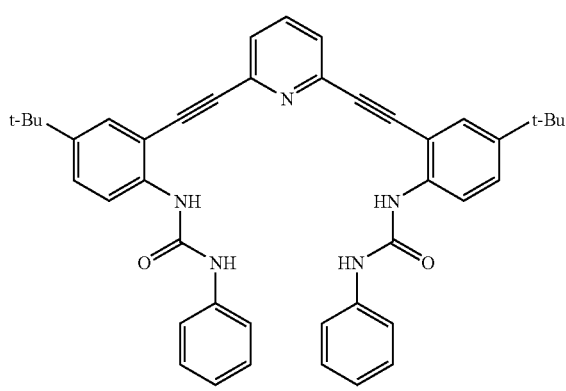

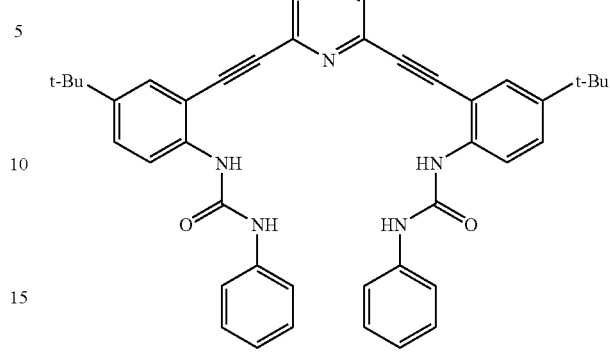

In one aspect, certain host compounds are represented by the formula

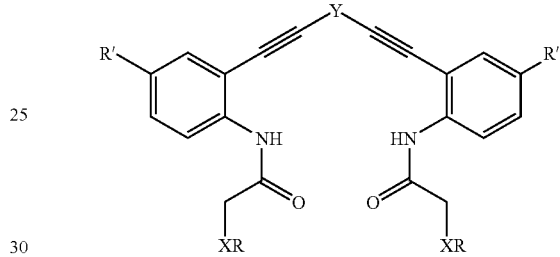

wherein X is O or S;

R is H, acyl, aralkyl or lower alkyl; and R' is H or lower alkyl, such as t-butyl. Examples of such compounds can be represented by the formula

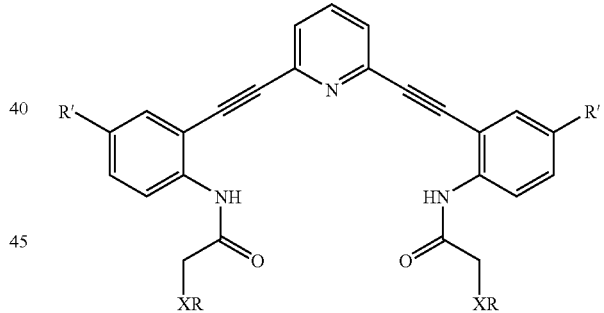

When X is O, the host compounds are particularly useful for binding oxophilic ions, such as calcium. Other host compounds having the formula above, wherein X is S have been designed to bind thiophilic metals. Examples of such compounds can be represented by the formula:

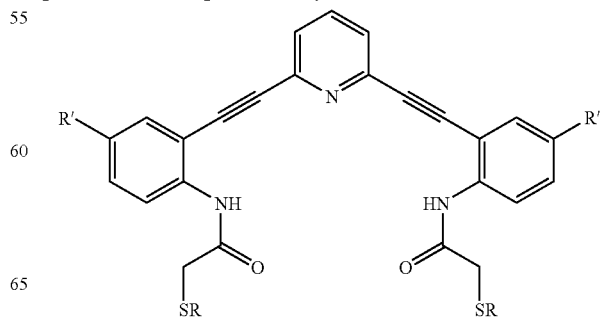

wherein R is H, acyl, aralkyl or lower alkyl; and R' is H, aliphatic, such as lower alkyl, aralkyl, aryl, sulfonyl, phosphonyl, phosphate, sulfate, —XC(O)OR$^6$ or —XC(O)NR$^7$R$^8$; wherein X is optional and if present is selected from the group consisting of —O—, —N(R$^9$)— or —S—; R$^6$ is selected from lower alkyl, aralkyl and aryl; and R$^7$, R$^8$ and R$^9$ independently are selected from H, lower alkyl, aralkyl and aryl. Particular examples of such compounds also can be represented by the formula

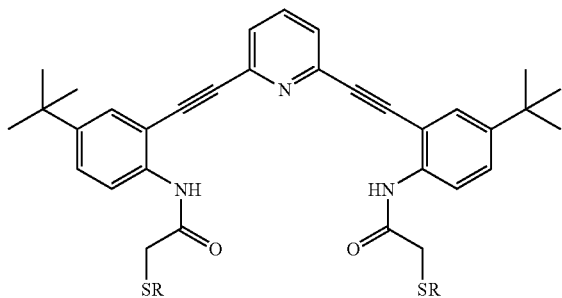

wherein R is H, acyl, aralkyl or lower alkyl.

Additional compounds useful for binding thiophilic metals include those of the formula

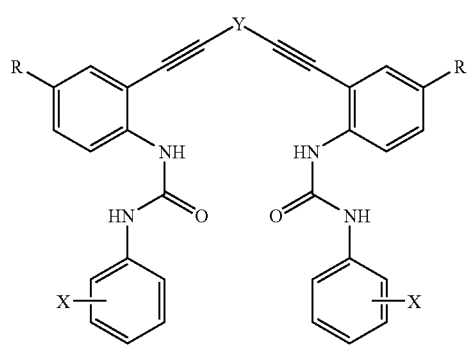

wherein X comprises an alkyl sulfide moiety.

Also disclosed herein are methods for making the disclosed receptor compounds as well as intermediates for preparing the receptors. One type of versatile intermediate employed in the synthesis of exemplary receptor compounds disclosed herein is represented by the formula

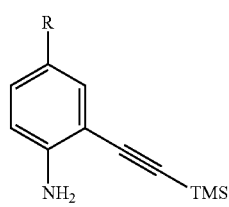

wherein R is H, lower alkyl, aralkyl or the like. Such compounds can be used to assemble (typically by an organometallic coupling reaction, such as a Sonogashira coupling) compounds of the formula

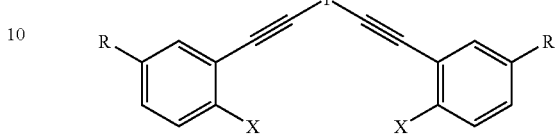

wherein X represents an aniline nitrogen, which optionally may be substituted. The aniline nitrogens can be converted into any one of many heteroatomic functional groups, including amides, sulfonamides, ureas, imines, and the like using standard synthetic techniques known to those of skill in the art of synthetic organic chemistry. The choice of group is dictated by several factors, including: optimizing guest interactions, changing the size of the binding cavity, preorganizing the binding cavity (by cyclization, for instance). Such factors are recognized and can be adjusted by those of skill in the art.

The disclosed host compounds are useful for binding and/or detecting ligands, in particular ionic ligands, including cationic and anionic ligands. The ligands may be inorganic or organic, but generally are inorganic. Typically, for binding anionic ligands, host compounds are protonated. Particular examples of anionic ligands bound and/or recognized by the disclosed host compounds include, without limitation sulfate, hydrogen sulfate, perchlorate or nitrate. Exemplary host compounds exhibit ligand binding selectivity or recognition. The host compounds may exhibit selectivity in binding of the ligand or reporting of a ligand's presence. For example, a spectral property of a host compound, such as fluorescence, may shift upon binding certain ligands, but not others. Examples of the disclosed host compounds have been designed to bind to salts containing particular metals, particularly toxic metals, including without limitation Pb, As, Zn, U, Ca, Cd and Hg.

It has been demonstrated for exemplary compounds disclosed herein that the spectral properties, such as the UV-Vis spectra shift noticeably upon binding of different guests. For example, the extended conjugation inherent in 2,6-bis(2-anilinoethynyl)pyridines derivatives produces distinct emission properties that will be used to monitor interactions with guest molecules. Exemplary compounds can distinguish between different anionic guests such as between Cl$^-$, which induces a shift in the UV-vis spectra of certain compounds, and Br$^-$, which does not induce such shifts. This discriminatory ability is most marked when the receptor is protonated. This indicates that these specific receptors can discriminate between different guests and are pH sensitive and can be tailored for use in solutions of specific acidity.

Reference will now be made in detail to the presently preferred embodiments of the disclosed compounds, compositions and methods.

EXAMPLES

The following examples are provided to illustrate certain particular features and/or embodiments. These examples should not be construed to limit the invention to the particular features or embodiments described.

Example 1

This example describes general materials and methods used in the synthesis and characterization of exemplary host compounds. All solvents were dried over 3 Å molecular sieves unless otherwise stated. THF, $Et_3N$, and $CH_2Cl_2$ were respectively distilled from potassium metal and $CaH_2$ prior to use. All other materials were obtained from TCI-America, Sigma-Aldrich, Acros and Strem and used as received. $^1H$ and $^{13}C$ NMR spectra were recorded using a Varian Inova 300 ($^1H$ 299.95 MHz, $^{13}C$ 75.43 MHz) or Inova 500 ($^1H$ 500.10 MHz, $^{13}C$ 125.75 MHz) spectrometer. Chemical shifts (δ) expressed as ppm downfield from tetramethylsilane using either the residual solvent peak as an internal standard ($CDCl_3$ $^1H$, 7.27 ppm) or using $CDCl_3$ spiked with 1% trimethylsilane for the $^1H$ NMR spectra. For the $^{13}C$ NMR spectra the middle $CDCl_3$ peak (δ 77.00 ppm) was used as the internal standard. Signal patterns are indicated as b, broad; s, singlet; d, doublet; t, triplet; m, multiplet. Coupling constants (J) are given in hertz. UV-Vis spectra were recorded using a Hewlett-Packard 8453 spectrophotometer and extinction coefficients are expressed in $M^{-1}$ $cm^{-1}$. Mass spectra were recorded using an Agilent 1100 Series LC/MSD. Emission spectra were recorded on a Hitachi F-4500 fluorescence spectrophotometer. Melting points were determined with a Meltemp II apparatus or a TA Instruments DSC 2920 Modulated DSC. Column chromatography was performed on Whatman reagent grade silica gel (230-400 mesh). Rotary chromatography was performed on a Harrison Research Chromatotron model 7924T with EM-Science 60 $PF_{254}$ silica gel. Precoated silica gel plates (Sorbent Technology, $UV_{254}$, 200 μm, 5×20 cm) were used for analytical thin-layer chromatography.

General Sulfonamide Synthesis: A general synthesis of sulfonamides followed the scheme:

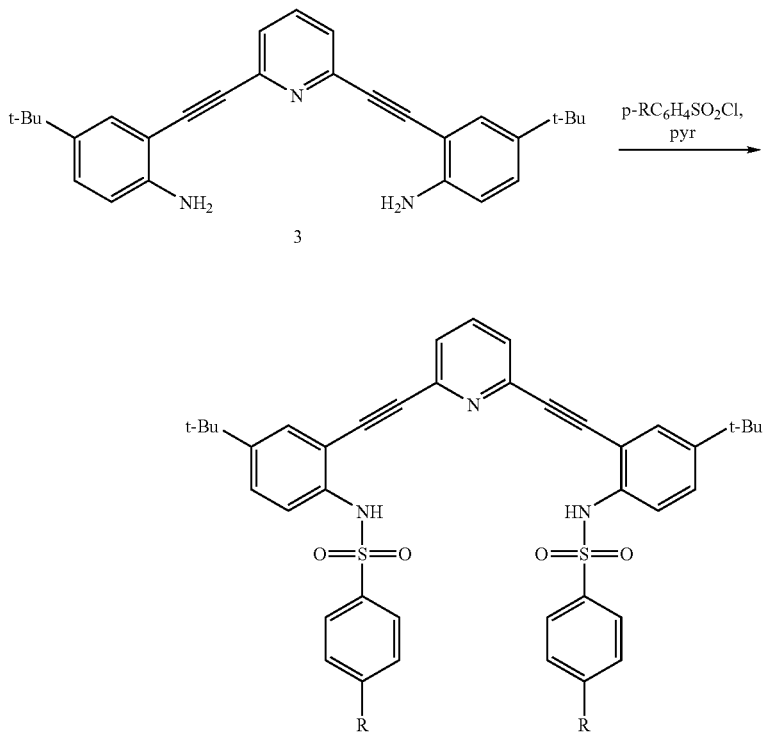

A solution of arene 3 (1 equiv) and sulfonyl chloride (5 equiv) in pyridine (8-15 mM) was stirred for 3 hours under an $N_2$ environment. Following concentration in vacuo, the crude oil was filtered through a 2.5 cm silica plug and then chromatographed on silica gel.

The synthesis of several exemplary sulfonamides by the general method is illustrated by the scheme:

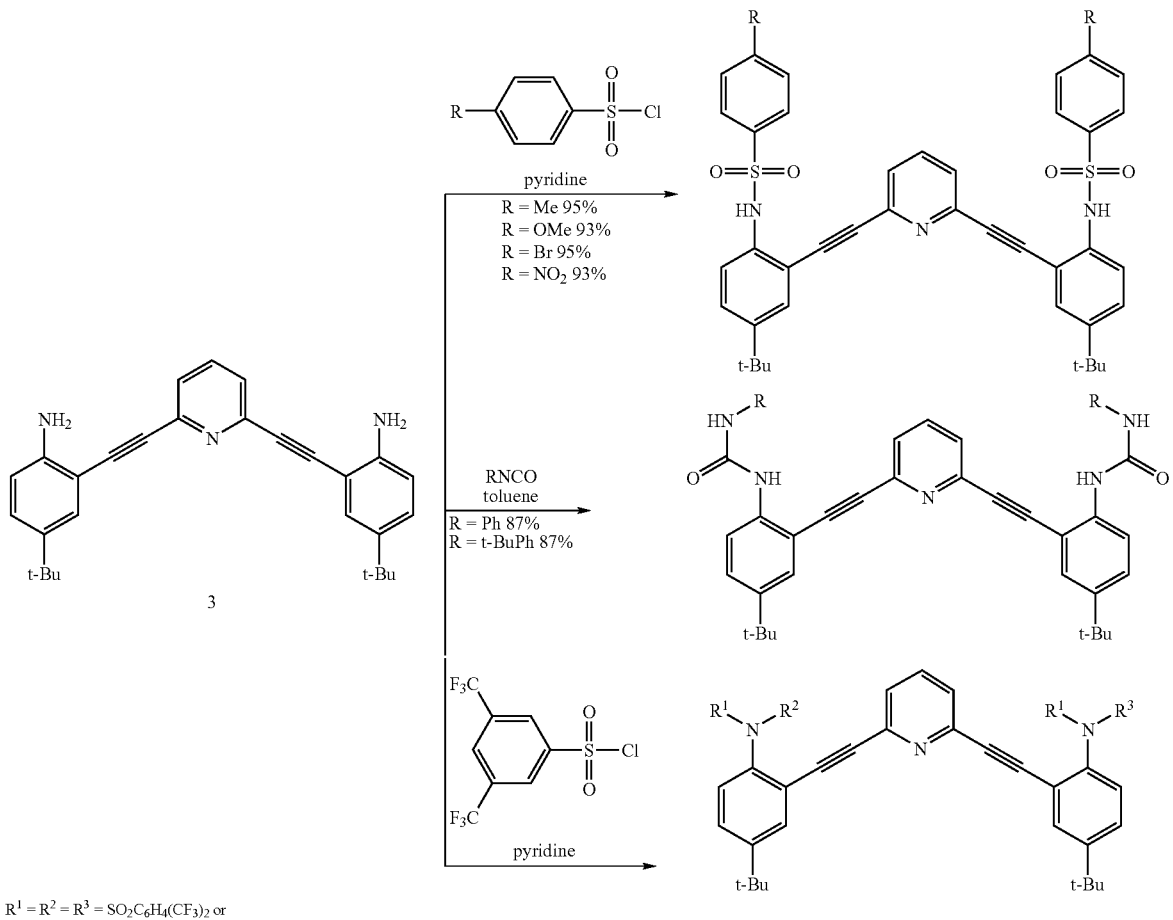

R¹ = R² = R³ = SO₂C₆H₄(CF₃)₂ or
R³ = H; R¹ = R² = SO₂C₆H₄(CF₃)₂

General salt preparation: A 10 mM stock solution of sulfonamide receptor dissolved in CDCl₃ with 1% TMS that had been passed through basic alumina and stored over 3 Å molecular sieves was prepared. With a 9 inch pipet and 10 ml pipet bulb HCl gas is passed through the sulfonamide solution 20 times. The resulting bright yellow solution is diluted to the original volume and an appropriate aliquot is removed for study.

Crystal growth conditions: Sulfonamide receptors were dissolved in a 10×75 mm test tube with EtOAc to a concentration >10 mM (for halide salts HX gas was passed through the EtOAc solution of receptor). Alternatively, 1 drop of concentrated HX is added and the resulting yellow solution is thoroughly mixed). Hexanes cooled to 0° C. were layered on top of receptor solutions and set aside. After 3 days colorless (neutral receptor complex) or yellow (protonated receptor complex) single crystals were harvested for X-ray diffraction studies.

Single Crystal X-ray Diffraction: X-Ray diffraction data for $(1.H_2O)_2$, $(2.H_2O)_2$, $(H2^+.Cl^-)_2$, $(H1^+.Cl^-).(1.H_2O)$ and $(H1^+.Br^-)_2$ were collected on a Bruker SMART APEX diffractometer using MoK$_\alpha$ radiation ($\lambda$=0.7107 Å). Data were corrected for absorption using the SADABS v2.02 area-detector absorption correction program. The structures were solved by direct methods and refined based on $|F|^2$. All non-hydrogen atoms were refined with anisotropic displacement parameters. Hydrogen atoms in the investigated structures were found from the residual density maps and refined with isotropic thermal parameters except those in terminal t-Bu groups in $(H2^+.Cl^-)_2$, $(H1^+.Cl^-).(1.H_2O)$ and $(H1^+.Br^-)_2$, which were placed in calculated positions and refined in a rigid group model with isotropic thermal parameters U(H)= 1.5 Ueq (C). One of the H atoms at the bridging solvent molecule in $(1.H_2O)_2$ is disordered over two positions in a 1:1 ratio. The O atoms of the bridging water molecule and the Cl atom in $(H1^+.Cl^-).(1.H_2O)$ are disordered over two positions corresponding to opposite orientations of the dimeric units. These O and Cl atoms were refined in the same positions with occupation factors $\mu$=½. The H atoms attached to the O atom in the bridging water molecules were not found from the F-map. All calculations were performed with the SHELXTL v.6.1 program package.

Example 2

This example describes the synthesis of sulfonamide compound 1 via the general synthesis set forth above.

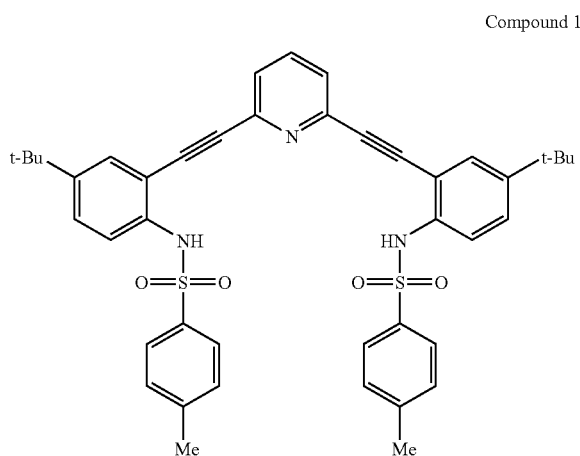

Compound 1

Arene 3 (150 mg, 0.36 mmol) was reacted with p-toluenesulfonyl chloride according to General Preparation for Sulfonamides (above). Purification by:chromatography (1:1 hexanes:EtOAc) afforded $(1.H_2O)_2$ (249 mg, 95%) as a pale yellow solid. Recrystallization by diffusion (hexanes:EtOAc) afforded colorless crystals. Mp: 133-135° C. $^1$H NMR (300 MHz, CDCl$_3$): δ 7.85-7.71 (m, 5H), 7.52-7.43 (m, 6H), 7.35 (dd, J=8.5, 2.3 Hz, 2H), 7.15 (d, J=8.5 Hz, 4H), 2.34 (s, 6H), 1.26 (s, 18H). $^{13}$C NMR (75 MHz, CDCl$_3$): δ 147.53, 143.73, 142.85, 136.93, 136.49, 135.84, 129.54 (2C), 127.89, 127.25, 126.29, 120.52, 112.89, 93.20, 85.56, 34.29, 31.03, 21.45. UV-Vis (CH$_2$Cl$_2$): λ$_{max}$ (ε) 234 (58,000), 287 (31,000), 330 (27,600) nm. Fluorescent emission ($[(1.H_2O)_2]\leq 0.057$ mM in CHCl$_3$; 354 nm excitation): λ$_{max}$ 388 nm. IR (neat): ν 3266, 2961, 2899, 2877, 2213, 1555, 1156 cm$^{-1}$. MS (CI pos) m/z (%): 732 (M$^+$+2, 21), 731 (MH$^+$, 56), 730 (M$^+$, 100); C$_{43}$H$_{43}$N$_3$O$_4$S$_2$ (729.95).

Example 3

This example describes the synthesis of sulfonamide compound 2 via the general synthesis set forth above.

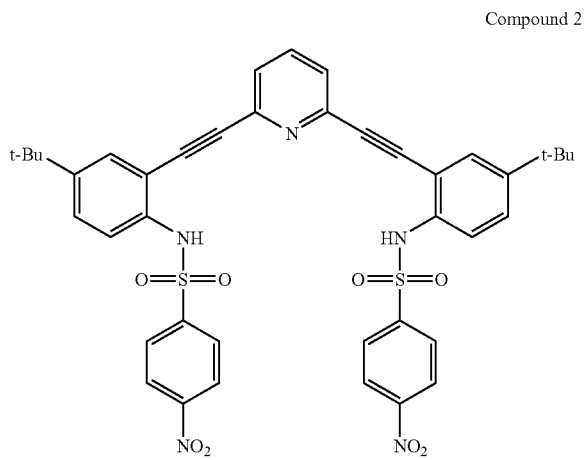

Compound 2

Arene 3 (150 mg, 0.36 mmol) was reacted with p-nitrobenzenesulfonyl chloride according to General Preparation for Sulfonamides (above). Purification by:chromatography (20:1 CH$_2$Cl$_2$:EtOAc) afforded $(2.H_2O)_2$ (285 mg, 93%) as a pale yellow solid. Recrystallization by diffusion (pentane:CHCl$_3$ or hexanes:EtOAc) afforded pale yellow crystals. Mp: 136-139° C. $^1$H NMR (300 MHz, CDCl$_3$): δ 8.15 (d, J=8.7 Hz, 4H), 8.03 (d, J=8.7 Hz, 4H), 7.74 (t, J=7.8 Hz, 1H), 7.55 (d, J=8.7 Hz, 2H), 7.48-7.37 (m, 6H), 1.29 (s, 18H). $^{13}$C NMR (75 MHz, CDCl$_3$): δ 150.10, 149.33, 145.32, 142.68, 137.20, 134.63, 129.82, 128.68, 128.28, 126.31, 124.12, 123.31, 114.59, 92.68, 85.71, 34.51, 31.05. UV-Vis (CH$_2$Cl$_2$): λ$_{max}$ (ε) 242 (56,200), 285 (35,500), 319 (23,000) nm. Fluorescent emission ($[(2.H_2O)_2]\leq 0.057$ mM in CHCl$_3$; 364 nm excitation): λ$_{max}$ 428 nm. IR (neat): ν 3271, 2964, 2869, 2213, 1348, 1171 cm$^{-1}$. MS (CI pos) m/z (%): 794 (M$^+$+2, 24), 793 (MH$^+$, 53), 792 (M$^+$, 100), 608 (17), 607 (44); C$_{41}$H$_{37}$N$_5$O$_8$S$_2$ (791.89).

Example 4

This example describes the synthesis of the para-methoxy analog of compounds 1 and 2. Arene 3 (110 mg, 0.26 mmol) was reacted with p-methoxybenzenesulfonyl chloride according to General Preparation for Sulfonamides (above). Purification by chromatography (20:1 CH$_2$Cl$_2$:EtOAc) afforded (pMeO.H$_2$O)$_2$ (185 mg, 93%) as a white crystalline solid. Recrystallization by diffusion (hexanes:CH$_2$Cl$_2$) afforded colorless crystals. Mp: 141-143° C. $^1$H NMR (300 MHz, CDCl$_3$): δ 7.77 (d, J=9 Hz, 4H), 7.76 (t, J=9 Hz, 1H), 7.53-7.45 (m, 5H), 7.37 (dd, J=9, 3 Hz, 2H), 6.84 (d, J=9 Hz, 4H), 3.77 (s, 6H), 1.28 (s, 18H). $^{13}$C NMR (75 MHz, CDCl$_3$): δ 163.06, 147.62, 142.93, 136.75, 135.70, 130.85, 129.60, 129.43, 127.85, 126.44, 120.64, 114.09, 113.02, 93.28, 85.33, 55.45, 34.31, 31.03. UV-Vis (CH$_2$Cl$_2$): λ$_{max}$ (ε) 239 (71,700), 292 (30,200), 343 (23,000) nm. Fluorescent emission ($[(pMeO.H_2O)_2]\leq 0.05$ mM in CHCl$_3$; 353 nm excitation): λ$_{max}$ 389 nm. IR (neat): ν 3248, 2962, 2902, 2870, 2214, 1498, 1161 cm$^{-1}$. MS (CI pos) m/z (%): 764 (M$^+$+2, 22), 763 (MH$^+$, 49), 762 (M$^+$, 100); C$_{43}$H$_{43}$N$_3$O$_6$S$_2$ (761.95).

Example 5

This example describes the characterization of the solid state and solution phase ion binding properties of exemplary host molecules disclosed herein. Colorless single crystals of compounds 1 and 2 suitable for X-ray diffraction were grown by layering hexane onto ethyl acetate solutions of each receptor. As suggested from the $^1$H NMR spectroscopic data, complexes (1.H$_2$O)$_2$ and (2.H$_2$O)$_2$ both crystallize as dimers in space group P-1 with two receptor molecules and two water molecules per unit cell; consequently, each dimer has crystallographic inversion symmetry. A prominent feature of each crystal structure is the presence of two hydrogen bonding water molecules stitching the receptor dimers together. Both pyridine nitrogens accept hydrogen bonds from a different water molecule [2.797(4)-2.804(2) Å, O—H . . . N angles 172(4)-175(3)°], while one water-water hydrogen bond is present [2.917(5)-3.006(7) Å, O—H . . . O angles 164(4)-178(6)°]. All of the N-substituted sulfonamides adopt the energetically most-favored 'staggered' conformation, and both sulfonamide protons on each receptor donate a hydrogen bond to a different water molecule [2.855(4)-2.860(3) Å, 157(2)-164(3)° and 3.028(4)-3.039(3) Å, 158(2)-164(3)°] such that the 2+2 dimer structure is held together by four sulfonamide-water hydrogen bonds, two pyridine-water hydrogen bonds, one water-water hydrogen bond and two π-stacking interactions between receptors ranging from 3.42-3.44 Å.

The dimerization of receptor 1 was further investigated in CDCl$_3$ solutions. Receptor 1 was dissolved in water-saturated CDCl$_3$ to a concentration of 197 mM. Monitoring the sulfonamide N—H and water $^1$H NMR resonances following a series of dilutions resulted in data that could be fit to a 1:1 dimerization with the non-linear regression curve fitting software WinEQNMR. In CDCl$_3$ solutions receptor 1 is shown to dimerize with a modest K$_{dim}$=42 M$^{-1}$. Supporting evidence of dimerization in CDCl$_3$ solutions resulted from the NOE observed between the protons on the guest water molecules and the sulfonamide protons of the receptor. Receptor 1 exhibits a propensity to crystallize as a dimer with H$_2$O even in the presence of other potential neutral guest molecules and in solvents dried over 3 Å molecular sieves.

Receptor molecules 1 and 2 both alter guest selectivity by simple changes in the protonation state of the receptors. By protonating the pyridine nitrogen of receptors 1 and 2, the anion binding capacity of these receptors is activated. The halide binding properties of H1$^+$ have been investigated in the solid state: single crystals of the chloride and bromide complexes are prepared by dissolving receptor 1 or 2 in ethyl acetate and bubbling HCl or HBr gas through the solution. Crystallization is induced by layering hexanes onto the yellow ethyl acetate solutions. Strikingly, the single crystal structures of the H2$^+$.Cl$^-$ and H1$^+$.Br$^-$ complexes revealed nearly isostructural dimers to those observed for the neutral (1.H$_2$O)$_2$ and (2.H$_2$O)$_2$ water dimers. In the solid state the (H2$^+$.Cl$^-$)$_2$ and (H1$^+$Br$^-$)$_2$ dimers (FIG. 2) are held together by four sulfonamide hydrogen bonds [3.156(2)-3.229(2) Å, N—H . . . Cl angles 151(2)-171(3)°; 3.338(5)-3.440(6) Å, N—H . . . Br angles 136(4)-168(4)°], two pyridinium N—H hydrogen bonds to the anions [3.022(2) Å, 175(3)° for (H2$^+$Cl$^-$)$_2$ and 3.127(6) Å, 173(4)° for (H1$^+$.Br$^-$)$_2$], two C$_{aryl}$—H . . . X hydrogen bonds (3.69-3.90 Å), and two π-stacking interactions between receptors (3.49 Å for (H2$^+$.Cl$^-$)$_2$ and 3.61 Å for (H1$^+$.Br$^-$)$_2$. The numerous hydrogen bonds and unique dimerization bring the negatively charged halides into close proximity with halide-halide distances of 3.92 Å for (H2$^+$.Cl$^-$)$_2$ and 4.08 Å for (H1$^+$.Br$^-$)$_2$.

CAChe semi-empirical calculations of the 2,6-bis(2-anilino-ethynyl)pyridine receptors suggested that larger polyatomic anions would not fit within the binding pocket of the receptor. As predicted, the single crystal X-ray structure of the HBF$_4$ salt (H1$^+$.BF$_4^-$) reveals that the binding pocket is too small to accommodate the interaction of the large BF$_4^-$ guest with either sulfonamide proton. Dilution experiments of H1$^+$.BF$_4^-$ revealed minimal change in the $^1$H NMR spectrum upon addition with CDCl$_3$, indicating negligible dimerization in solution as predicted by the receptor conformation observed in the crystal structure. However, titrations of H1$^+$BF$_4^-$ with tetra-n-butylammonium halide salts do indicate anion binding occurs in solution between the receptor and halides. Furthermore, the concentration dependence observed in the $^1$H NMR spectrum upon dilution of (H1$^+$.Cl$^-$)$_2$ in CDCl$_3$ indicates the presence of a receptor/halide dimer in solution. A supersaturated solution of (H1$^+$.Cl$^-$)$_2$ (60 mM) was obtained by passing HCl gas through a CDCl$_3$ solution of neutral receptor 1. Plotting the changes in chemical shift upon dilution and subsequent fitting of this data to a 1:1 dimerization model with the non-linear least squares regression program WinEQNMR resulted in a K$_{dim}$=250 M$^{-1}$ in CDCl$_3$.

Further evidence of dimerization was obtained by mixing a 1:1 ratio of receptor 1 and a p-methoxyphenyl sulfonamide derivative (synthesis described in Example 4 above). In an equimolar mixture of the two receptors, the resulting $^1$H NMR signals are shifted from the signals observed for either of the analogous homodimers prepared in the same way at the same concentration. Briefly, the equimolar mixtures of these receptors were prepared at 10 mM in CDCl$_3$ as follows: [1.H$_2$O].[pMeO.H$_2$O]. 1.H$_2$O (3.650 mg, 0.00488 mmol) and pMeO.H$_2$O (3.740 mg, 0.00480 mmol) were dissolved in seperate portions of CDCl$_3$ with 1% TMS (1 mL) passed through basic alumina and dried with 3 Å molecular sieves. Aliquots (400 μL) from each solution were transfered to an NMR tube via syringe and thoroughly mixed. $^1$H NMR spectra were recorded on a Varian 300 MHz spectrometer. Proton signals were referenced to the 1% TMS included in the CDCl$_3$. $^1$H NMR (300 MHz, CDCl$_3$): δ 7.81-7.73 (m, 10H), 7.52-7.44 (m, 12H), 7.38-7.33 (m, 8H), 7.18 (d, J=9 Hz, 4H), 6.85 (d, J=9 Hz, 6H), 7.18 (d, J=6 Hz, 3H) 2.29 (s, 6H), 1.26 (s, 18H).

By comparison, 10 mM stock solutions of (H1$^+$.Cl$^-$)$_2$ had the data: $^1$H NMR (300 MHz, CDCl$_3$): δ 9.51 (b, 2H), 8.40 (b, 1H), 8.13 (d, J=6 Hz, 4H), 8.00-7.75 (b, 4H), 7.48-7.41 (m, 6H), 7.18 (d, J=6 Hz, 3H) 2.29 (s, 6H), 1.26 (s, 18H). 10 mM stock solutions of (HpMeO$^+$.Cl$^-$)$_2$ had the data: $^1$H NMR (300 MHz, CDCl$_3$): δ 9.36 (b, 2H), 8.31 (t, 1H), 8.17 (d, J=9 Hz, 4H), 7.72 (d, J=9 Hz, 4H), 7.40 (m, 6H), 6.86 (d, J=9 Hz, 4H) 3.75 (s, 6H), 1.26 (s, 18H).

This result suggests that both homodimers and a third species—the heterodimer—are present in solution, but equilibrating quickly on the NMR timescale. From all of these experiments it is evident that dimerization of both the neutral and protonated forms of 2,6-bis(2-anilinoethynyl)pyridine receptors occurs both in the solid state and in solution.

Remarkably, a different type of "heterodimer" (H1$^+$.Cl$^-$).(1.H$_2$O) was also crystallized in the presence of concentrated HCl with one water and one chloride in the binding pocket. Briefly, the heterodimer [H1$^+$.Cl$^-$].[HpMeO$^+$.Cl$^-$] was prepared as follows: The stock solutions from the preparation of [1.H$_2$O].[pMeO.H$_2$O] (above) were combined and protonated with HCl gas (see above, General salt preparation). $^1$H NMR spectra were recorded on a Varian 300 MHz spectrometer. Proton signals were referenced to the 1% TMS included in the CDCl$_3$. $^1$H NMR (300 MHz, CDCl$_3$): δ 9.49 (s, 2H), 9.44 (s, 2H), 8.30 (b, 2H), 8.18 (d, J=9 Hz, 4H), 8.12 (d, J=9 Hz, 4H), 7.71 (d, J=6 Hz, 4H) 7.46 (m, 12H), 7.17 (d, J=6 Hz, 4H), 6.85 (d, J=6 Hz, 4H), 3.73 (s, 6H), 2.27 (s, 6H), 1.25 (s, 36H). The resultant heterodimer contains one protonated receptor that binds a chloride anion while the other receptor in the dimer is neutral and bound to a water molecule. Water and chloride are freely exchangeable in this binding pocket and provide intermediate structural features to the H$_2$O and halide dimers. Analogous to the other dimers presented, the heterodimer is stabilized by π-stacking interactions between the two receptors (3.43 Å) and a series of seven guest assisted hydrogen bonds. Each guest molecule—water and chloride—accepts two sulfonamide N—H hydrogen bonds (3.157(3)-3.181(3) Å, N—H . . . X angles 158(3)-167(3)°) and additionally forms a helical hydrogen bonding pattern running between the pyridinium, chloride, water and pyridine heteroatoms (2.926(3)-3.10 Å, 164(3)-176(4)°). Two C$_{aryl}$—H.Cl hydrogen bonds (3.76-3.93 Å) also stabilize the dimer.

Example 6

This example describes the synthesis of the compound

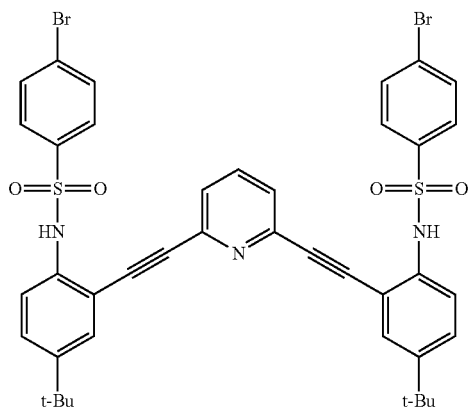

via the General Preparation for Sulfonamides described above. Briefly, arene 3 (100 mg, 0.24 mmol) was reacted with p-bromobenzenesulfonyl chloride. Purification by chromatography (2.5:1 hexanes:EtOAc) followed by recrystallization by diffusion (hexanes:EtOAc) afforded 10c (183 mg, 89%) as colorless crystals. Mp: 152-154° C. $^1$H NMR (300 MHz, CDCl$_3$): δ 8.00 (br s, 2H), 7.82-7.71 (m, 5H), 7.53-7.37 (m, 10H), 1.29 (s, 18H). $^{13}$C NMR (75 MHz, CDCl$_3$): δ 148.25, 142.72, 138.65, 137.16, 135.52, 132.22, 129.59, 128.88, 128.18, 127.96, 126.19, 121.56, 113.46, 92.97, 85.89, 34.43, 31.08. Fluorescence emission ([10c]≦5.7×10$^{-5}$ M in CHCl$_3$; 308 nm excitation): λ$_{max}$ 381 nm. MS (CI pos) m/z (%): 863 (M$^+$+6, 24), 862 (M$^+$+5, 61), 861 (M$^+$+4, 42), 860 (M$^+$+3, 100), 859 (M$^+$+2, 21), 858 (MH$^+$); C$_{41}$H$_{37}$Br$_2$N$_3$O$_4$S$_2$ (857.06).

Example 7

This example describes the synthesis of the compound

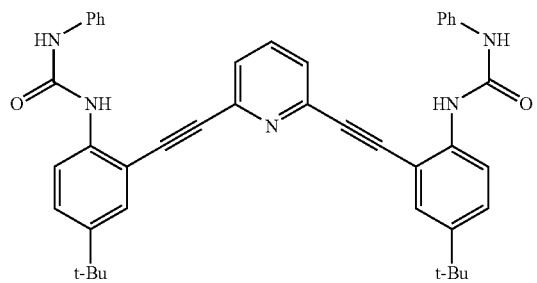

Phenyl isocyanate (303 mg, 2.5 mmol) was added to a solution of arene 3 (215 mg, 0.5 mmol) in toluene (25 mL). The reaction was stirred for 12 hours under an N$_2$ environment. Concentration in vacuo afforded a crude oil which was filtered through a 2.5 cm silica plug with 1:1 hexanes:EtOAc. Chromatography on silica gel (3:1 hexanes:EtOAc) followed by precipitation with hexanes or ether afforded the desired product (287 mg, 87%) as a white, fluffy solid. Recrystallization by diffusion (pentane:CHCl$_3$) afforded white, needle crystals. Mp: 212-215° C. $^1$H NMR (300 MHz, CDCl$_3$): δ 8.32 (br s, 2H), 8.07 (d, J=4.8 Hz, 2H), 7.74 (br s, 2H), 7.47-7.28 (m, 11H), 7.15 (t, J=4.5 Hz, 4H), 6.92 (t, J=4.5 Hz, 2H), 1.29 (s, 18H). $^{13}$C NMR (125 MHz, THF-d$_8$): δ 152.95, 145.38, 144.62, 141.17, 140.40, 138.15, 130.11, 129.56, 128.78, 127.65, 122.94, 120.33, 114.49, 110.45, 94.38, 87.33, 35.01, 31.75. Fluorescence emission ([11a]≦5.7×10$^{-5}$ M in CHCl$_3$; 371 nm excitation): λ$_{max}$ 411 nm. MS (CI pos) m/z (%): 661 (MH$^+$, 49), 660 (M$^+$, 100); C$_{43}$H$_{41}$N$_5$O$_2$ (659.82).

Example 8

This example describes the synthesis of the compound

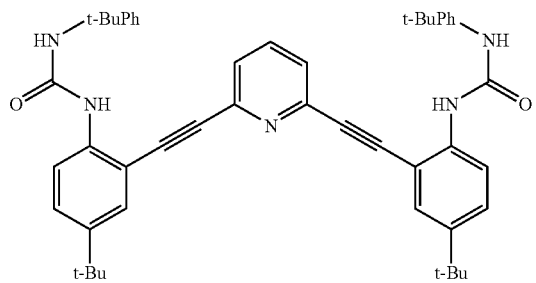

4-(t-Butyl)phenyl isocyanate (124 mg, 0.72 mmol) was added to a solution of arene 3 (100 mg, 0.24 mmol) in toluene (10 mL). The reaction was stirred for 12 hours under an N$_2$ environment. Concentration in vacuo followed by chromatography on silica gel (CHCl$_3$) and trituration with acetone or ether afforded 11b (135 mg, 75%) as a white, fluffy solid. Mp: 197-200° C. $^1$H NMR (300 MHz, CDCl$_3$): δ 8.33 (br s, 2H), 8.05 (d, J=8.7 Hz, 2H), 7.66 (s, 2H), 7.38-7.15 (m, 15H), 1.28 (s, 18H), 1.23 (s, 18H). MS (CI pos) m/z (%): 774 (MH$^+$+1, 13), 773 (MH$^+$, 66), 772 (M$^+$, 100); C$_{51}$H$_{57}$N$_5$O$_2$ (772.03).

Example 9

This example describes the synthesis of thiol-based receptors via the scheme:

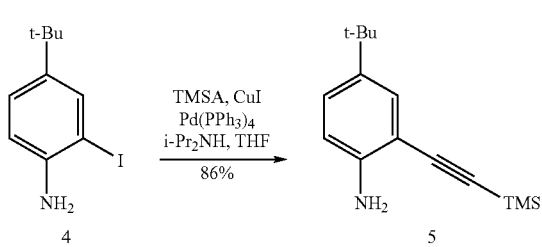

1. K$_2$CO$_3$, MeOH, THF
2. 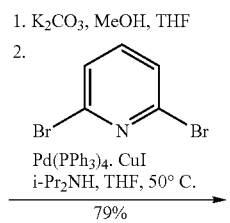

Pd(PPh$_3$)$_4$, CuI
i-Pr$_2$NH, THF, 50° C.

79%

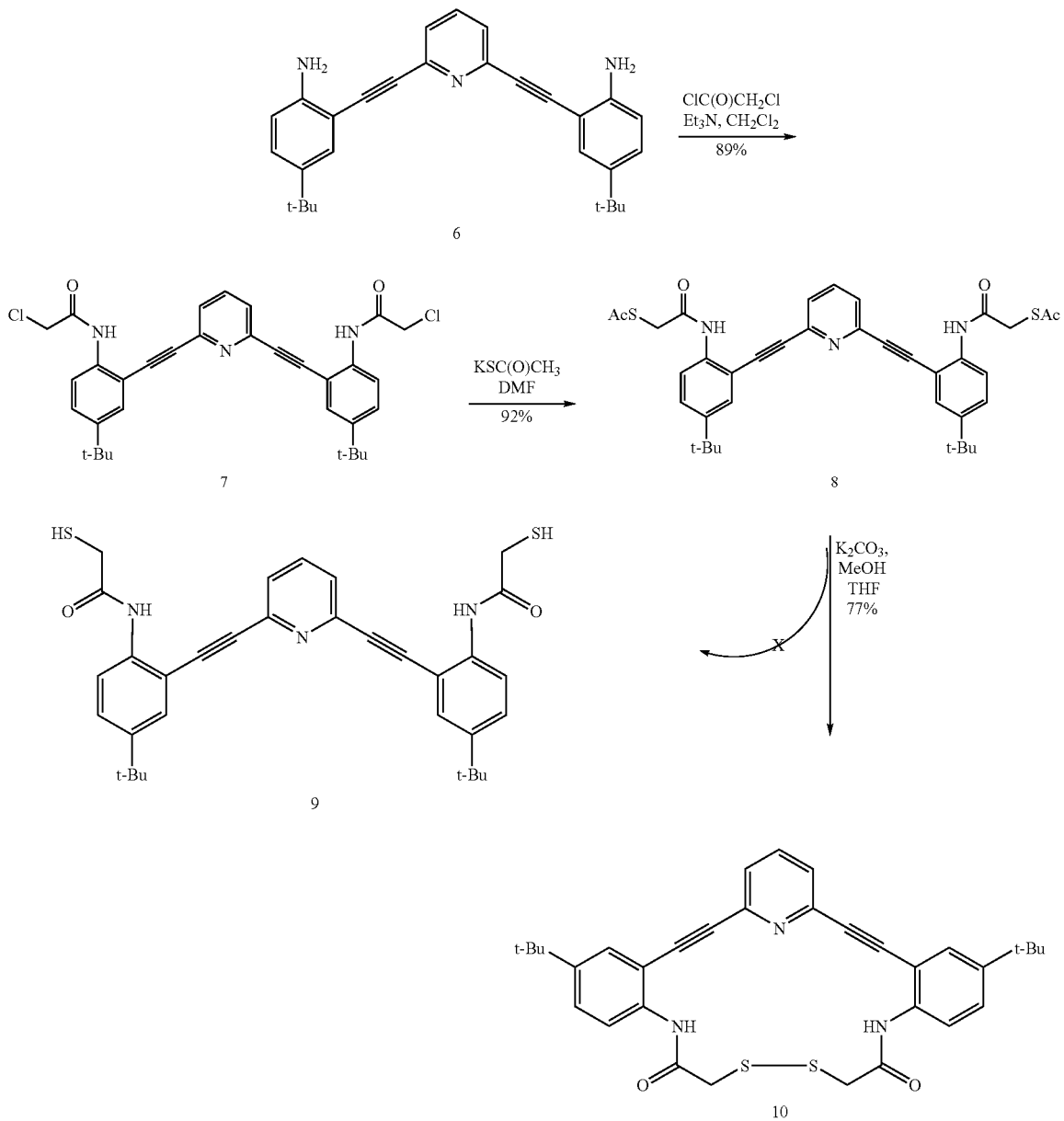

With continued reference to the scheme above, synthesis began with previously reported iodoaniline 4, (Wan, W. B.; Haley, M. M. *J. Org. Chem.* 2001, 66, 3893-3901) available in 73% yield via iodination of tert-butylaniline. Pd-catalyzed cross-coupling (*Metal-Catalyzed Cross-Coupling Reactions*, 2nd ed.; de Meijere, A., Diederich, F., Eds.; Wiley-VCH: Weinheim, 2004) of 4 with TMSA afforded ethynylarene 5 in 86% yield. Arene 6 was obtained in 79% yield by desilylation of 5 with weak base (*Protecting Groups in Organic Synthesis*, 3rd ed.; Greene, T. W.; Wuts, P. G. M., Eds.; Wiley-VCH: New York, 1999; pp 654-657) followed by two-fold cross-coupling to 2,6-dibromopyridine. Treatment of diamine 6 with an excess of chloroacetylchloride in $CH_2Cl_2$ afforded diamide 7 in very good yield. Reaction of arene 7 with potassium thioacetate in DMF (van Bommel, K. J. C.; de Jong, M. R.; Metselaar, G. A.; Verboom, W.; Huskens, J.; Hulst, R.; Kooijman, H.; Spek, A. L.; Reinhoudt, D. N. *Chem. Eur. J.* 2001, 7, 3603-3615) resulted in acetyl-protected receptor 8. Crystals of arene 8 suitable for single crystal X-ray diffraction, obtained from slow diffusion of hexanes into a concentrated solution of 8 in EtOAc, indicated a dimeric association with intermolecular H-bonding. Treatment of 8 with $K_2CO_3$ in MeOH and THF under both air-free and ambient conditions afforded the intramolecular disulfide analog 10 in 77% yield instead of the free thiol 9. The disulfide bond of 10 enforces a pre-organization of the phenylacetylene substituents with the amide-N, disulfide linkage, and pyridine-N in a potential binding cavity.

An alternate synthetic route for receptor 9 was investigated following the scheme:

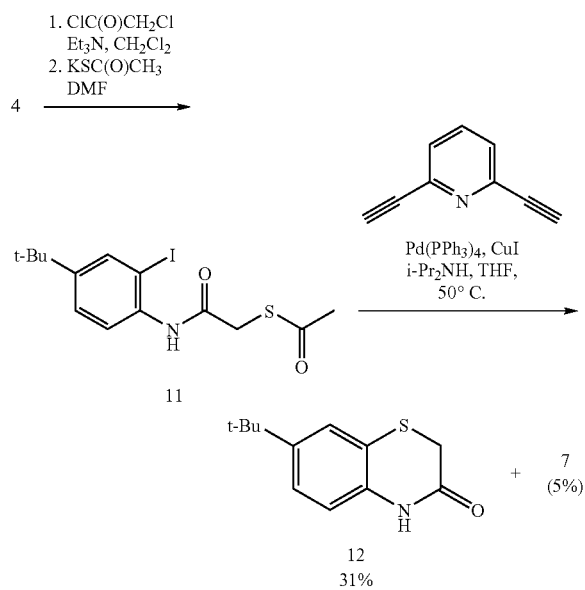

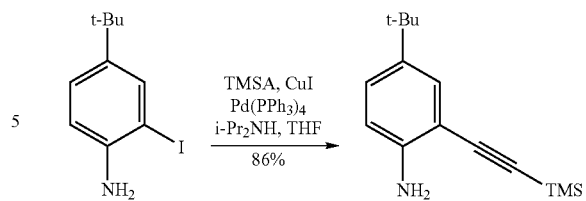

Successive treatment of iodoarene 4 with chloroacetylchloride and potassium thioacetate afforded intermediate 11. Pd-catalyzed cross-coupling of 11 to 2,6-diethynylpyridine (Dana, B. H.; Robinson, B. H.; Simpson, J. *J. Organomet. Chem.* 2002, 648, 251-269) produced penultimate 8 in very low yield (5%) due to competitive formation of benzothiazinone 12 from iodoarene 11. Both slow addition of the diethynylpyridine to a solution of 11 as well as direct combination of the two starting materials resulted in similar product distribution, with 12 as the major product. Benzothiazinone formation can be rationalized by pyridine base or metal catalyst deprotection of the thiol moiety followed by nucleophilic displacement of the iodide, a prearranged and favorable formation of an unsaturated six-membered ring. Conversion of 11 to 12 effectively prevented further cross coupling to the central pyridine core and hence resulted in low yield for arene 8. The remainder of the product distribution could not be discerned but likely included disulfide and/or oligomeric analogs of both 10 and 11.

Absorption and emission data: Compounds 6-8 and 10 are fluorescent chromophores that exhibit blue or purple fluorescence under UV light (365 nm). The absorption spectra of compounds 6-8 and 10 are dominated by a characteristic pattern consisting of three peaks. There is a lack of significant spectral changes associated with conversion of diamide 8 to disulfide 10, which is not unexpected, as overall conjugation remains limited by the methylene spacer. Upon addition of TFA, 10 displayed enhanced low energy absorption (>100 nm) as well as conversion from a colorless solution with purple fluorescence to a deep yellow solution with yellow fluorescence. Treatment of the acidic solution with aqueous base resulted in return of the original absorption spectrum and fluorescence of 10.

Example 10

This example describes the synthesis and characterization of 4-tert-Butyl-2-(2-trimethylsilylethynyl)aniline 14 via the scheme:

A suspension consisting of 4-tert-butyl-2-iodoaniline 13 (800 mg, 2.9 mmol), Pd(PPh$_3$)$_4$ (168 mg, 0.15 mmol), and CuI (55 mg, 0.29 mmol) in i-Pr$_2$NH (50 mL) and THF (50 mL) was degassed by bubbling Ar. TMSA (1.3 mL, 9 mmol) was added and the suspension was stirred at room temperature for 12 hours under N$_2$. The suspension was filtered and the insoluble salts washed twice with Et$_2$O. The filtrate was combined with the Et$_2$O washes, concentrated, and purified by Chromatotron (3:2 hexanes:CH$_2$Cl$_2$) to afford 14 (611 mg, 86%) as a red-brown oil. $^1$H NMR (300 MHz, CDCl$_3$): δ 7.32 (d, J=2.1 Hz, 1H), 7.17 (dd, J=8.4, 2.1 Hz, 1H), 6.65 (d, J=8.4 Hz, 1H), 4.13 (br s, 2H), 1.27 (s, 9H), 0.29 (s, 9H). $^{13}$C NMR (75 MHz, CDCl$_3$): δ 145.87, 140.55, 128.68, 127.21, 114.09, 107.25, 102.40, 98.99, 33.79, 31.33, 0.16. IR (neat) ν 3476, 3381, 2960, 2868, 2147, 1500 cm$^{-1}$. MS (CI pos) m/z (%): 316 (M++THF, 38), 279 (M$^+$+Na$^+$, 35), 247 (M$^+$+2, 23), 246 (MH$^+$, 100); C$_{15}$H$_{23}$NSi (245.44).

Example 11

This example describes the synthesis and characterization of the compound referred to above as arene 3:

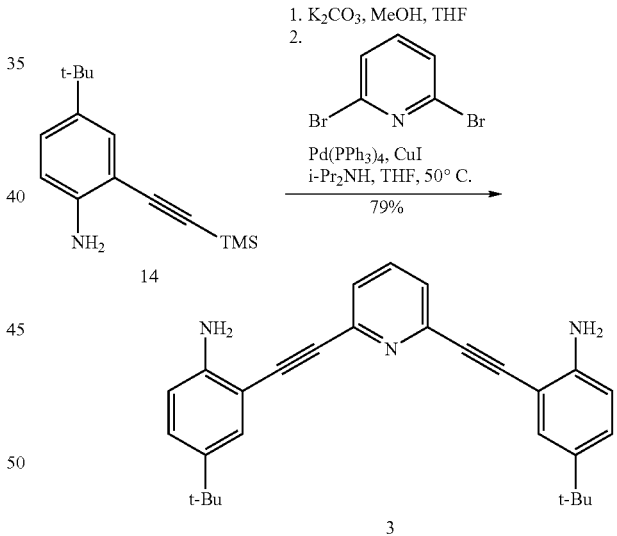

A suspension of ethynylarene 14 (206 mg, 0.84 mmol) and K$_2$CO$_3$ (5 equiv.) in MeOH (20 mL) and Et$_2$O (10 mL) was stirred at room temperature and monitored by TLC until completion (15-30 min). The solution was diluted with Et$_2$O and washed with water and brine. The organic layer was dried over MgSO$_4$ and concentrated in vacuo. Without further purification, the residue was dissolved in THF (10 mL) and added dropwise over a period of 12 hours to a stirred, deoxygenated suspension of 2,6-dibromopyridine (50 mg, 0.21 mmol), Pd(PPh$_3$)$_4$ (25 mg, 0.02 mmol), and CuI (8 mg, 0.04 mmol) in THF (50 mL) and i-Pr$_2$NH (50 mL) at 45° C. After an additional 3 hours of stirring, the suspension was filtered and the insoluble salts washed twice with Et$_2$O. The filtrate was combined with the Et$_2$O washes, concentrated, and purified by Chromatotron (3:2 hexanes:EtOAc) to afford 3 (70 mg, 79%) as a pale brown, crystalline solid. Mp: 226° C. $^1$H NMR (300 MHz, CDCl$_3$): δ 7.64 (t, J=8.1 Hz, 1H), 7.45-7.43 (m, 4H), 7.20 (dd, J=8.7, 1.8 Hz, 2H), 6.67 (d, J=8.7 Hz, 2H), 4.35 (br s, 4H), 1.27 (s, 18H). $^{13}$C NMR (75 MHz, CDCl$_3$): δ 146.31, 143.84, 140.56, 136.36, 129.24, 128.04, 125.73, 114.34, 105.82, 93.11, 87.59, 33.85, 31.31. IR (neat) ν 3451, 3355, 2957, 2866, 2199, 1500 cm$^{-1}$. UV/vis (CH$_2$Cl$_2$): λ$_{max}$ (ε) 249 (44,200), 295 (24,300), 359 (22,500) nm. MS (CI pos) m/z (%): 423 (M$^+$+2, 100), 422 (MH$^+$, 100); C$_{29}$H$_{31}$N$_3$ (421.58).

Example 12

This example describes the synthesis and characterization of the compound referred to above as arene 7:

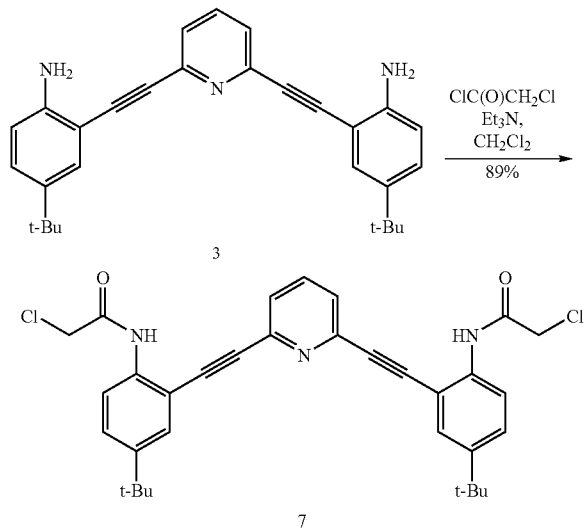

A solution of chloroacetylchloride (571 mg, 5.1 mmol) in CH$_2$Cl$_2$ (10 mL) was added to a stirred, deoxygenated solution of arene 3 (395 mg, 0.94 mmol) and Et$_3$N (379 mg, 3.76 mmol) in CH$_2$Cl$_2$ (10 mL). The reaction was stirred for 12 hours at room temperature under N$_2$ and then concentrated in vacuo. CH$_2$Cl$_2$ was added and the organic layer was washed thrice with water, dried over MgSO$_4$, and concentrated in vacuo. The crude material was filtered through a 2.5 cm silica plug (1:1 hexanes:EtOAc) and concentrated to afford 4 (476 mg, 89%) as a pale brown solid. Mp: 193° C. $^1$H NMR (300 MHz, CDCl$_3$): δ 9.23 (br s, 2H), 8.30 (d, J=8.3 Hz, 2H), 7.72 (t, J=8.3 Hz, 1H), 7.64 (d, J=2.1 Hz, 2H), 7.52 (d, J=8.1 Hz, 2H), 7.43 (dd, J=8.1, 2.1 Hz, 2H), 4.27 (s, 4H), 1.31 (s, 18H). $^{13}$C NMR (75 MHz, CDCl$_3$): δ 163.62, 147.46, 143.19, 136.83, 135.83, 129.32, 127.87, 126.20, 119.07, 111.15, 94.78, 84.80, 43.21, 34.41, 31.10. IR (neat) ν 3363, 2962, 2868, 2207, 1691, 1523 cm$^{-1}$. UV/vis (CH$_2$Cl$_2$): λ$_{max}$ (ε) 254 (52,600), 293 (27,700), 335 (27,600) nm. MS (CI pos) m/z (%): 578 (M$^+$+4, 15), 577 (M$^+$+3, 23), 576 (M$^+$+2, 75), 575 (MH$^+$, 38), 574 (M$^+$, 100); C$_{33}$H$_{33}$Cl$_2$N$_3$O$_2$ (574.54).

Example 13

This example describes the synthesis and characterization of the compound referred to above as arene 8:

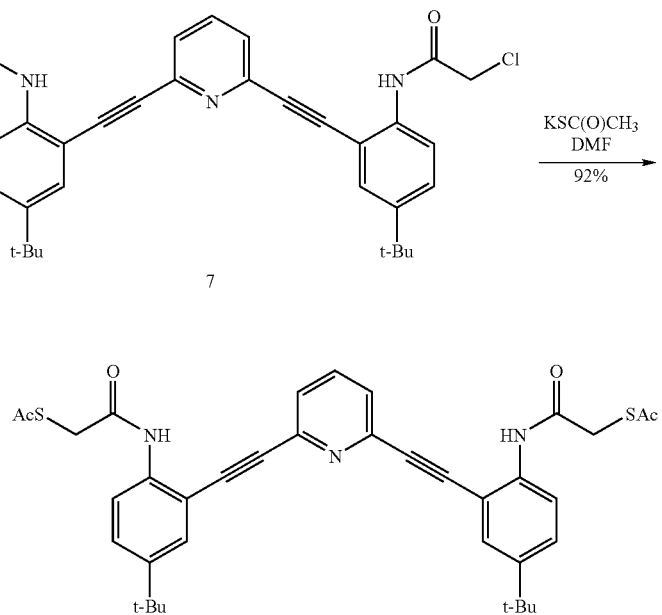

Potassium thioacetate (16 mg, 0.14 mmol) was added to a stirred, deoxygenated solution of arene 7 (34 mg, 0.06 mmol) in DMF (3 mL). The reaction was stirred for 12 hours at room temperature under $N_2$ and then concentrated in vacuo. The crude material was filtered through a 2.5 cm silica plug (1:1 hexanes:EtOAc) and purified via Chromatotron (2:1 hexanes: EtOAc) to afford 8 (35 mg, 92%) as a spongy light yellow solid. Recrystallization by diffusion (hexanes:EtOAc) afforded colorless crystals. Mp: 94° C. $^1$H NMR (300 MHz, $CDCl_3$): δ 8.75 (br s, 2H), 8.28 (d, J=8.7 Hz, 2H), 7.75 (s, 3H), 7.58 (d, J=2.4 Hz, 2H), 7.39 (dd, J=8.7, 2.4 Hz, 2H), 3.76 (s, 4H), 2.34 (s, 6H), 1.28 (s, 18H). $^{13}$C NMR (75 MHz, $CDCl_3$): δ 195.20, 166.16, 146.81, 143.31, 136.59, 136.54, 129.38, 127.68, 126.57, 119.45, 110.79, 94.31, 85.15, 34.27, 33.99, 31.05, 30.13. IR (neat) ν 3339, 3058, 2962, 2868, 2208, 1693, 1518 $cm^{-1}$. UV/vis ($CH_2Cl_2$): $\lambda_{max}$ (ε) 253 (48,200), 291 (24,500), 330 (21,600) nm. MS (CI pos) m/z (%): 656 ($M^+$+2, 19), 655 ($MH^+$, 44), 654 ($M^+$, 100); $C_{37}H_{39}N_3O_4S_2$ (653.85).

Example 14

This example describes the synthesis and characterization of the compound referred to above as disulfide 10.

matotron (3:2 hexanes:EtOAc) afforded 10 (17 mg, 77%) as a crystalline, white solid. Mp: 247° C. $^1$H NMR (300 MHz, $CDCl_3$): δ 9.79 (br s, 2H), 8.47 (d, J=9 Hz, 2H), 7.72 (t, J=7.7 Hz, 1H), 7.57 (d, J=2.1 Hz, 2H), 7.51 (d, J=8.1 Hz, 2H), 7.46 (dd, J=8.8, 2.1 Hz, 2H), 3.70 (s, 4H), 1.58 (s, 2H), 1.34 (s, 18H). IR (neat) ν 3318, 2959, 2925, 2855, 2207, 1687, 1515 $cm^{-1}$. UV/vis ($CH_2Cl_2$): $\lambda_{max}$ (ε) 254 (52,200), 296 (24,800), 323 (17,800), 337 (17,500) nm. MS (CI pos) m/z (%): 570 ($M^+$+1, 19), 569 ($MH^+$, 38), 568 ($M^+$, 100); $C_{33}H_{33}N_3O_2S_2$ (567.76).

Alternate route product, benzothiazinone 12

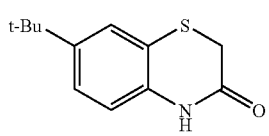

had the spectral data $^1$H NMR (300 MHz, $CDCl_3$): δ 7.30 (d, J=1.2 Hz, 1H), 7.18 (dd, J=4.8, 1.2 Hz, 1H), 6.82 (d, J=4.8 Hz,

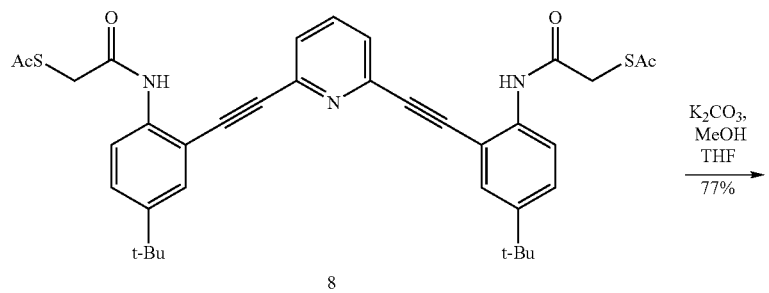

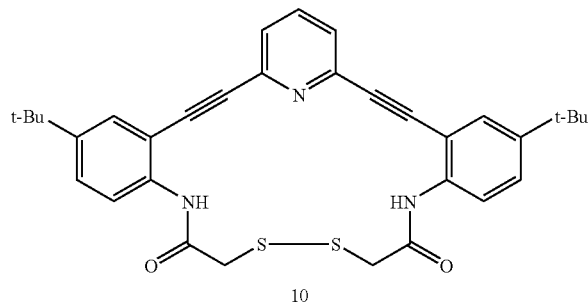

$K_2CO_3$ (3 equiv) was added to a deoxygenated solution of 8 (23 mg, 0.03 mmol) in MeOH (5 mL) and THF (3 mL). The suspension was stirred at room temperature under $N_2$ for 30 minutes and completion was monitored by TLC. $Et_2O$ was added and the reaction mixture was washed with water and/or a saturated solution of $NH_4Cl$. The aqueous layer was further washed with $Et_2O$ twice. The organics were combined and dried over $MgSO_4$. Concentration and purification via Chro- 1H), 3.43 (s, 2H), 1.29 (s, 9H). MS (CI pos) m/z (%): 279 ($M^+$+$H_2O$+$CH_3CN$, 100), 263 ($M^+$+$CH_3CN$, 73), 218 ($M^+$- 3, 61); $C_{12}H_{15}NOS$ (221.32).

Example 15

This example describes the synthesis of host compounds according to the scheme:

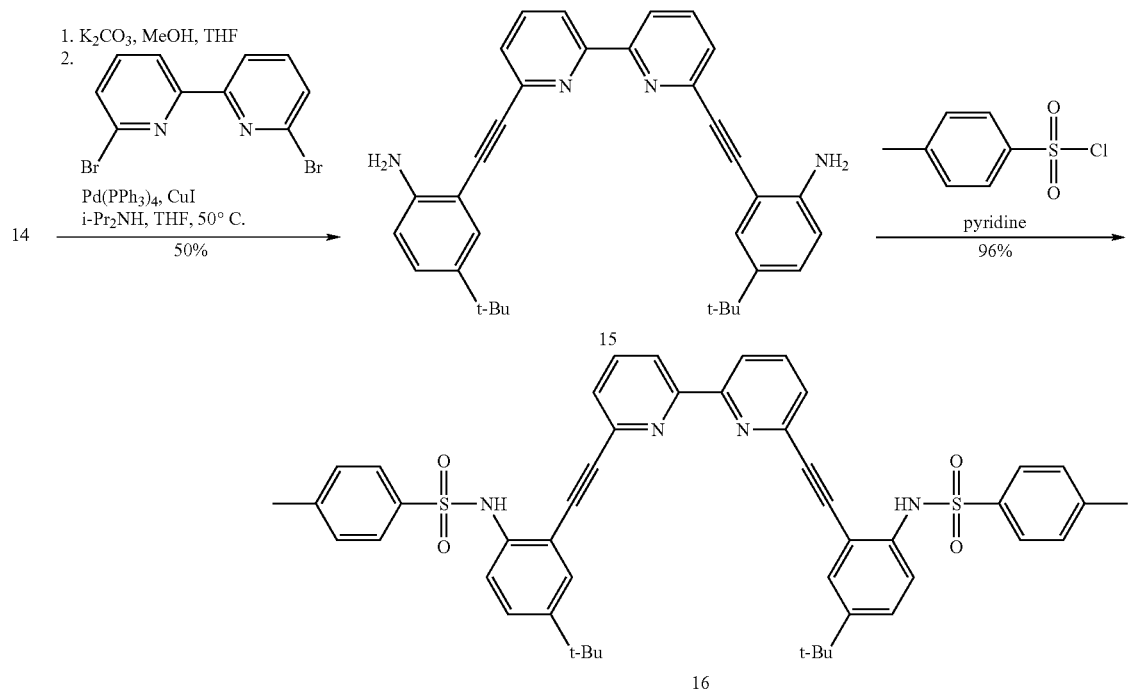

A suspension of ethynylarene 14 (391 mg, 1.6 mmol) and $K_2CO_3$ (5 equiv.) in MeOH (20 mL) and $Et_2O$ (10 mL) was stirred at room temperature and monitored by TLC until completion (15-30 minutes). The solution was diluted with $Et_2O$ and washed with water and brine. The organic layer was dried over $MgSO_4$ and concentrated in vacuo. Without further purification, the residue was dissolved in THF (10 mL) and added dropwise over a period of 12 hours to a stirred, deoxygenated suspension of 6,6'-dibromo-2,2'-dipyridyl (200 mg, 0.64 mmol), $Pd(PPh_3)_4$ (173 mg, 0.2 mmol), and CuI (60 mg, 0.3 mmol) in THF (100 mL) and i-$Pr_2NH$ (100 mL) at 50° C. After an additional 3 hours of stirring, the suspension was concentrated and filtered through a 2.5 cm silica plug (1:1 hexanes:EtOAc). Purification by column chromatography ($CH_2Cl_2$) afforded 15 (159 mg, 50%) as a bright yellow, crystalline solid. $^1H$ NMR (300 MHz, $CDCl_3$): δ 8.45 (d, J=7.2 Hz, 2H), 7.81 (t, J=8.1 Hz, 2H), 7.55 (d, J=8.1 Hz, 2H), 7.48 (d, J=2.3 Hz, 2H), 7.22 (dd, J=8.4, 2.3 Hz, 2H), 6.70 (d, J=8.4 Hz, 2H), 4.29 (br s, 4H), 1.30 (s, 18H).

Arene 15 (25 mg, 0.05 mmol) was reacted with p-toluenesulfonyl chloride according to General Preparation of Sulfonamides. Chromatography on silica gel (3:1 hexanes:EtOAc) afforded 16 (38 mg, 96%) as a pale yellow solid. Recrystallization by diffusion (hexanes:EtOAc) afforded colorless crystals. Mp: 251-252° C. $^1H$ NMR (300 MHz, $CDCl_3$): δ 8.58 (d, J=7.8 Hz, 2H), 7.90 (t, J=7.8 Hz, 2H), 7.77 (d, J=8.4 Hz, 4H), 7.58-7.42 (m, 8H), 7.37 (dd, J=8.8, 2.4 Hz, 2H), 7.14 (d, J=7.8 Hz, 4H), 2.32 (s, 6H), 1.29 (s, 18H). $^{13}C$ NMR (125 MHz, $CDCl_3$): δ 155.86, 147.77, 143.85, 141.95, 137.44, 136.36, 135.74, 129.54, 129.18, 127.75, 127.40, 127.29, 121.15, 120.63, 113.34, 94.77, 84.26, 34.40, 31.13, 21.52. Fluorescence emission ([16]≦5.7×10$^{-5}$ M in $CHCl_3$; 343 nm excitation): $\lambda_{max}$ 390 nm. MS (CI pos) m/z (%): 809 ($M^+$+2, 29), 808 ($MH^+$, 63), 807 ($M^+$, 100); $C_{48}H_{46}N_4O_4S_2$ (807.03).

Example 16

This example describes the synthesis of host compounds according to the scheme:

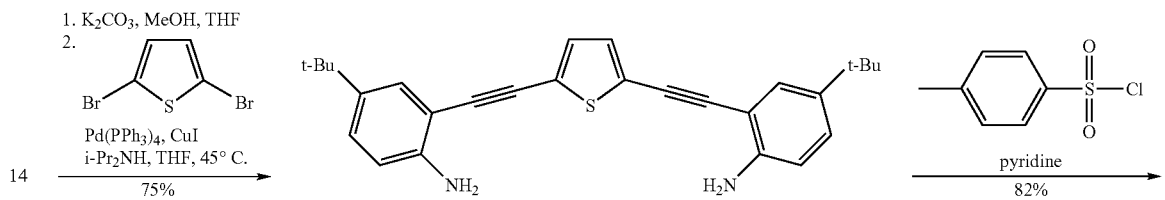

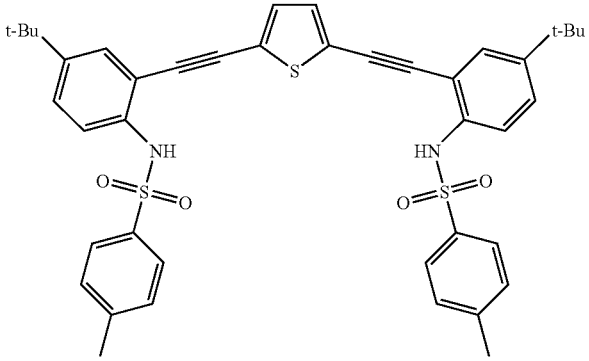

18

A suspension of ethynylarene 14 (500 mg, 2 mmol) and K$_2$CO$_3$ in MeOH (20 mL) and Et$_2$O (10 mL) was stirred at room temperature and monitored by TLC until completion (15-30 minutes). The solution was diluted with Et$_2$O and washed with water and brine. The organic layer was dried over MgSO$_4$ and concentrated in vacuo. Without further purification, the residue was dissolved in THF (10 mL) and added dropwise over a period of 12 hours to a stirred, deoxygenated suspension of 2,5-dibromothiophene (225 mg, 0.93 mmol), Pd(PPh$_3$)$_4$ (231 mg, 0.2 mmol), and CuI (76 mg, 0.4 mmol) in THF (50 mL) and i-Pr$_2$NH (50 mL) at 45° C. After an additional 3 hours of stirring, the suspension was concentrated and filtered through a 2.5 cm silica plug (CH$_2$Cl$_2$). Purification by column chromatography (CH$_2$Cl$_2$) afforded 17 (297 mg, 75%) as a bright yellow, crystalline solid. $^1$H NMR (300 MHz, CDCl$_3$): δ7.37 (d, J=2.1 Hz, 2H), 7.21 (dd, J=8.5, 2.1 Hz, 2H), 7.15 (s, 2H), 6.68 (d, J=8.5 Hz, 2H), 4.16 (br s, 4H), 1.29 (s, 18H). $^{13}$C NMR (75 MHz, CDCl$_3$): δ 145.52, 140.92, 131.49, 128.62, 127.63, 124.52, 114.38, 106.67, 91.25, 86.75, 33.89, 31.33. MS (CI pos) m/z (%): 498 (M$^+$+2+THF, 18), 497 (MH$^+$+THF, 100), 428 (M$^+$+2, 18), 427 (MH$^+$, 53); C$_{28}$H$_{30}$N$_2$S (426.21).

A solution of arene 17 (90 mg, 0.2 mmol) was reacted with p-toluenesulfonyl chloride according to General Preparation of Sulfonamides. Chromatography on silica gel (CH$_2$Cl$_2$) afforded 18 (123 mg, 82%) as a pale yellow solid. Mp: 89-91° C. $^1$H NMR (300 MHz, CDCl$_3$): δ 7.68 (d, J=8.7 Hz, 4H), 7.54 (d, J=8.4 Hz, 2H), 7.39-7.34 (m, 4H), 7.22 (d, J=8.7 Hz, 4H), 7.16 (s, 2H), 7.03 (s, 2H), 2.38 (s, 6H), 1.28 (s, 18H). $^{13}$C NMR (75 MHz, CDCl$_3$): δ 147.99, 144.00, 136.21, 134.96, 132.48, 129.66, 128.98, 127.63, 127.20, 124.09, 120.98, 113.79, 89, 54, 87.36, 34.39, 31.10, 21.58. UV/vis (CH$_2$C$_2$): λ$_{max}$ (ε) 234 (58,000), 287 (31,000), 330 (27,600) nm. Fluorescence emission ([18]≦5.7×10$^{-5}$ M in CHCl$_3$; 289 nm excitation): λ$_{max}$ 424 nm. MS (CI pos) m/z (%): 807 (M$^+$+2+THF, 16), 806 (MH$^+$+THF, 38), 805 (M$^+$+THF, 63), 737 (M$^+$+2, 21), 736 (MH$^+$, 37), 735 (M$^+$, 71), 595 (100), 580 (89); C$_{42}$H$_{42}$N$_2$O$_4$S$_3$ (734.99).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound or salt thereof comprising the formula

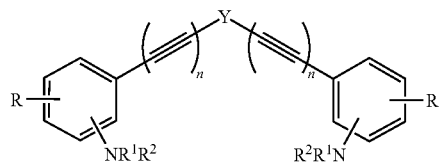

wherein Y is

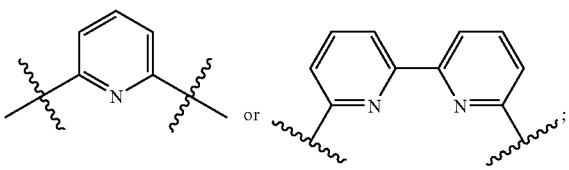

n is 1 or 2;

R is H or lower alkyl;

R$^1$ is H, lower alkyl or aralkyl;

R$^2$ is selected from H, acyl, aralkyl, phosphonyl, —SO$_2$R$^3$; —(R$^4$)C(O)R$^5$; —N(R$^6$)C(O)OR$^7$, and —N(R$^8$)C(O)NR$^9$R$^{10}$; and R$^3$; R$^4$; R$^5$; R$^6$; R$^7$; R$^8$; R$^9$ and R$^{10}$ independently are selected from H, lower alkyl, aralkyl, and aryl.

2. A compound or salt thereof comprising the formula

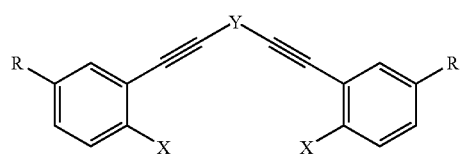

wherein Y is a pyridine or bipyridine;

R is selected from H and lower alkyl; and

X is selected from —N(H)SO$_2$R$^3$; —N(R$^4$)C(O)R$^5$; —N(R$^6$)C(O)OR$^7$; and —N(R$^8$)C(O)NR$^9$R$^{10}$;

R$^3$; R$^4$; R$^5$; R$^6$; R$^7$; R$^8$; R$^9$; and R$^{10}$ independently are selected from H, lower alkyl, aralkyl, and aryl.

3. A compound or salt thereof comprising the formula

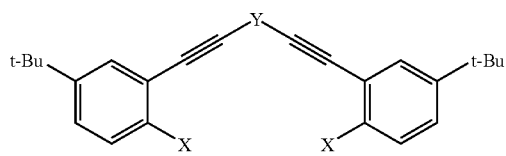

wherein Y is a pyridine or bipyridine:
X is selected from —N(H)SO$_2$R$^3$; —N(R$^4$)C(O)R$^5$; —N(R$^6$)C(O)OR$^7$; and —N(R$^8$)C(O)NR$^9$R$^{10}$; and
R$^3$; R$^4$; R$^5$; R$^6$; R$^7$; R$^8$ R$^9$ and R$^{10}$ independently are selected from H, lower alkyl, aralkyl, and aryl.

4. A compound or salt thereof comprising the formula

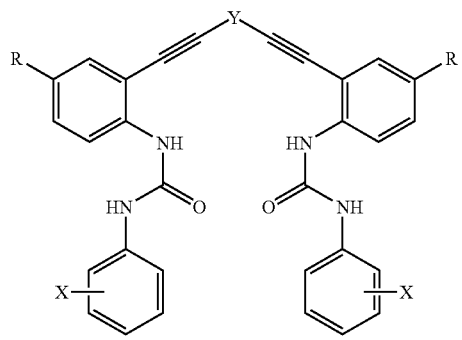

wherein Y is a pyridine or bipyridine:
R is lower alkyl;
X is halogen, —OR$^{11}$, alkyl sulfide, nitro, sulfonyl, phosphonyl, phosphate, sulfate, or lower alkyl;
and R$^{11}$ is H, acyl, or optionally substituted lower alkyl.

5. The compound of claim 4, wherein X comprises an —OR$^{11}$ or alkyl sulfide moiety, where R$^{11}$ is optionally substituted lower alkyl.

6. The compound of claim 5, wherein X has the formula —OR$^{11}$ or alkyl sulfide and R$^{11}$ is lower alkyl.

7. The compound of claim 3, having the formula

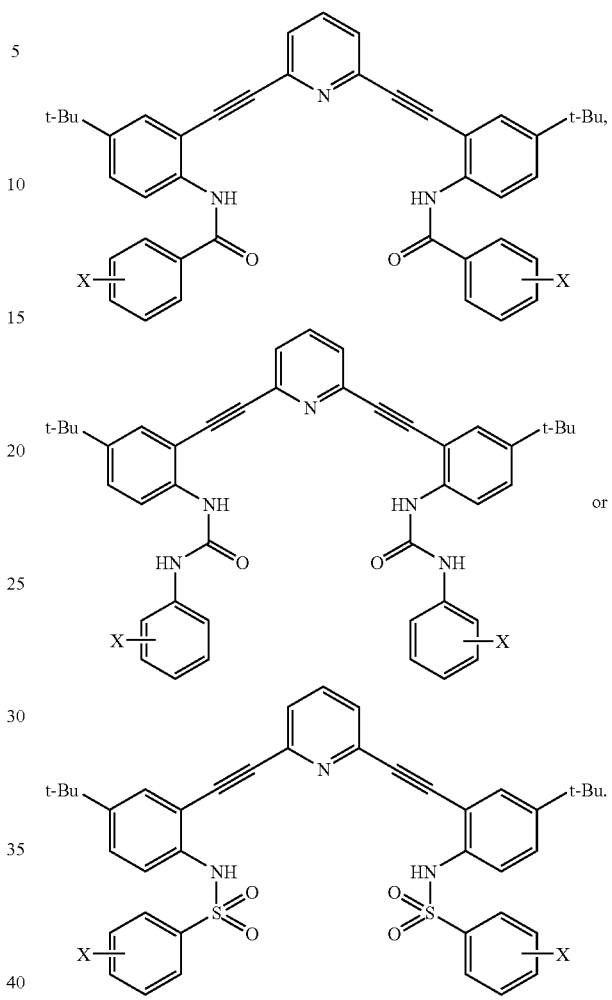

* * * * *